(12) United States Patent
Stucke et al.

(10) Patent No.: US 7,550,444 B2
(45) Date of Patent: Jun. 23, 2009

(54) COMPOSITION AND METHOD FOR PREPARING BIOCOMPATIBLE SURFACES

(75) Inventors: Sean M. Stucke, Farmington, MN (US); Ralph A. Chappa, Prior Lake, MN (US); Joseph A. Chinn, Shakopee, MN (US); Aron B. Anderson, Minnetonka, MN (US)

(73) Assignee: SurModics, Inc., Eden Prairie, MN (US)

( * ) Notice: Subject to any disclaimer, the term of this patent is extended or adjusted under 35 U.S.C. 154(b) by 653 days.

(21) Appl. No.: 11/090,655

(22) Filed: Mar. 25, 2005

(65) Prior Publication Data

US 2005/0244453 A1    Nov. 3, 2005

Related U.S. Application Data

(60) Provisional application No. 60/556,634, filed on Mar. 26, 2004, provisional application No. 60/568,021, filed on May 3, 2004, provisional application No. 60/640,602, filed on Dec. 31, 2004, provisional application No. 60/567,915, filed on May 3, 2004.

(51) Int. Cl.
*A61K 31/727* (2006.01)
*A61K 47/00* (2006.01)
*A61F 2/00* (2006.01)

(52) U.S. Cl. .................. 514/56; 514/772.2; 514/772.4; 514/784; 424/423

(58) Field of Classification Search .................. 514/56, 514/772.2, 724.4, 784; 424/423
See application file for complete search history.

(56) References Cited

U.S. PATENT DOCUMENTS

| | | | |
|---|---|---|---|
| 5,002,582 A | 3/1991 | Guire et al. | |
| 5,252,701 A | 10/1993 | Jarrett et al. | |
| 5,348,873 A * | 9/1994 | Matsuda et al. | 435/182 |
| 5,350,800 A | 9/1994 | Verhoeven et al. | |
| 5,414,075 A | 5/1995 | Swan et al. | |
| 5,443,458 A | 8/1995 | Eury | |
| 5,563,056 A * | 10/1996 | Swan et al. | 435/180 |
| 5,637,460 A | 6/1997 | Swan et al. | |
| 5,714,360 A | 2/1998 | Swan et al. | |
| 5,788,979 A | 8/1998 | Alt et al. | |
| 6,120,536 A | 9/2000 | Ding et al. | |
| 6,214,901 B1 | 4/2001 | Chudzik et al. | |
| 6,231,600 B1 | 5/2001 | Zhong | |
| 6,299,604 B1 | 10/2001 | Ragheb et al. | |
| 6,387,379 B1 | 5/2002 | Goldberg et al. | |
| 6,503,538 B1 | 1/2003 | Chu et al. | |
| 6,509,104 B2 | 1/2003 | Huang et al. | |
| 6,559,132 B1 | 5/2003 | Holmer et al. | |
| 6,599,558 B1 | 7/2003 | Al-Lamee et al. | |
| 6,600,010 B2 | 7/2003 | Mao et al. | |
| 6,620,194 B2 | 9/2003 | Ding et al. | |
| 6,656,206 B2 | 12/2003 | Corcoran et al. | |
| 6,669,980 B2 | 12/2003 | Hansen | |
| 6,669,994 B2 | 12/2003 | Swan et al. | |
| 6,702,850 B1 * | 3/2004 | Byun et al. | 623/1.44 |
| 6,713,119 B2 | 3/2004 | Hossainy et al. | |
| 6,759,054 B2 | 7/2004 | Chen et al. | |
| 2001/0007083 A1 | 7/2001 | Roorda | |
| 2001/0029351 A1 | 10/2001 | Falotico et al. | |
| 2002/0087123 A1 | 7/2002 | Hossainy et al. | |
| 2002/0165608 A1 * | 11/2002 | Llanos et al. | 623/1.45 |
| 2002/0188037 A1 | 12/2002 | Chudzik et al. | |
| 2003/0059631 A1 | 3/2003 | Al-Lamee | |
| 2003/0161938 A1 | 8/2003 | Johnson | |
| 2003/0165613 A1 | 9/2003 | Chappa et al. | |
| 2004/0005470 A1 | 1/2004 | Koulik | |
| 2004/0047911 A1 | 3/2004 | Lyu et al. | |
| 2005/0004663 A1 | 1/2005 | Llanos et al. | |
| 2005/0060028 A1 | 3/2005 | Horres et al. | |
| 2005/0232970 A1 | 10/2005 | Stucke et al. | |

FOREIGN PATENT DOCUMENTS

| | | |
|---|---|---|
| EP | 0923953 | 6/1999 |
| EP | 0950386 | 10/1999 |
| EP | 0568310 | 11/1999 |
| WO | WO98/36784 | 8/1998 |
| WO | WO99/64086 | 12/1999 |
| WO | WO03/030879 | 4/2003 |
| WO | WO03/105920 | 12/2003 |
| WO | WO2004/075943 | 10/2004 |

OTHER PUBLICATIONS

Clapper, D.L, et al. (1995) *Mater. Technol.* 10:147-149.
Nakayama, Y, et al. (2002) *J Biomed Mater Res* 64A:52-61.

\* cited by examiner

*Primary Examiner*—Raymond J Henley, III
(74) *Attorney, Agent, or Firm*—Kagan Binder, PLLC

(57) ABSTRACT

The invention provides methods and compositions for providing biocompatible surfaces to medical articles. In particular the invention provides biocompatible coatings with heparin activity. In some aspects, the biocompatible coatings of the invention are able to release a bioactive agent. The coatings can be formed using biostable or biodegradable polymeric material and photoreactive groups. The invention also provides methods for improving the quality of bioactive agent-containing coatings by performing pre-irradiation of biocompatible coating compositions.

22 Claims, No Drawings

COMPOSITION AND METHOD FOR PREPARING BIOCOMPATIBLE SURFACES

CROSS-REFERENCE TO RELATED APPLICATION

The present non-provisional Application claims the benefit of commonly owned provisional Application having Ser. No, 60/556,634, filed on Mar. 26, 2004, and entitled PROCESS AND SYSTEMS FOR BIOCOMPATIBLE SURFACES; commonly owned provisional Application having Ser. No. 60/568,021, filed on May 3, 2004, and entitled COMPOSITION AND METHOD FOR PREPARING BIOCOMPATIBLE SURFACES; commonly owned provisional Application having Ser. No. 60/640,602, filed on Dec. 31, 2004 and entitled COMPOSITION AND METHOD FOR PREPARING SURFACES WITH BIOCOMPATIBILITY; and commonly owned provisional Application having Ser. No. 60/567,915, filed on May 3, 2004, and entitled DRUG RELEASE COATING WITH BLOOD COMPATIBLE POLYMERIC TOPCOAT, which Applications are incorporated herein by reference in their entirety.

FIELD OF THE INVENTION

The invention relates to preparation of biocompatible surfaces. More particularly, the invention relates to preparing biocompatible surfaces by disposing a composition that includes a biocompatible agent on a surface of a medical article. In addition, the invention relates to compositions that include a biocompatible agent and coating compounds that have incorporated the biocompatible agent.

BACKGROUND OF THE INVENTION

Recently, the use of drug-eluting stents (DES) in percutaneous coronary interventions has received much attention. DES are medical devices that present or release bioactive agent into their surroundings (for example, luminal walls or coronary arteries). Generally speaking, bioactive agent can be coupled to the surface of a medical device by surface modification, embedded and released from within polymer materials (matrix-type), or surrounded by and released through a carrier (reservoir-type). The polymer materials in such applications should optimally act as a biologically inert barrier and not induce further inflammation within the body. However, the molecular weight, porosity of the polymer, a greater percentage of coating exposed on the medical device, and the thickness of the polymer coating can contribute to adverse reactions to the medical device.

Improved compatibility with blood is a desired feature for a variety of medical devices that contact blood during clinical use. The materials used for manufacture of medical devices are not inherently compatible with blood and its components, and the response of blood to a foreign material can be aggressive, resulting in surface induced thrombus (clot) formation. This foreign body response can in turn impair or disable the function of the device and, most importantly, threaten patient health. It is often desirable to modify the surface of medical devices, such as DES, to provide a biocompatible surface, to minimize or avoid such adverse foreign body responses.

As used herein, a surface of a medical article is characterized as "biocompatible" if it is capable of functioning or existing in contact with biological fluid and/or tissue of a living organism with a net beneficial effect on the living organism. Long-term biocompatibility is desired for the purpose of reducing disturbance of a host organism. One approach to improved biocompatibility for medical device surfaces is to attach various biomolecules such as antithrombogenic agents, anti-restenotic agents, cell attachment proteins, growth factors, and the like, to the surface of the device. For example, antithrombogenic agents can reduce the generation of substances as part of the clotting cascade, antirestenotic agents can reduce generation of aggressive scar tissue growth around the device, while cell attachment proteins can contribute to the growth of a layer of endothelial cells around the device.

Several benefits can be provided by biocompatible medical device surfaces. For example, such surfaces can increase patient safety, improve device performance, reduce adherence of blood components, inhibit blood clotting, keep device surfaces free of cellular debris, and/or extend the useable lifetime of the device.

One biomolecule that has been utilized to improve biocompatibility of medical device surfaces is heparin. Heparin is a pharmaceutical that has been used clinically for decades as an intravenous anticoagulant to treat inherent clotting disorders and to prevent blood clot formation during surgery and interventional procedures. Heparin molecules are polysaccharides with a unique chemical structure that gives them specific biological activity. When heparin is immobilized onto the surface of a medical device material, it can improve the performance of the material when in contact with blood in several ways: 1) it can provide local catalytic activity to inhibit several enzymes critical to the formation of fibrin (which holds thrombi together); 2) it can reduce the adsorption of blood proteins, many of which lead to undesirable reactions on the device surface; and 3) it can reduce the adhesion and activation of platelets, which are a primary component of thrombus.

In addition to heparin, other biomolecules that can be provided on a medical device to improve biocompatibility include extracellular matrix (ECM) proteins or ECM peptides derived from these proteins. Surfaces modified with appropriate proteins or peptides are less likely to be recognized as foreign than the original device surface and will promote the attachment and overgrowth of specific desirable cell types.

The preparation of biocompatible surfaces, however, can be challenging. This is particularly the case when attempting to provide biocompatibility to devices that also have other properties, such as DES. Materials that are used to form these coating may not be inherently compatible with each other, thereby making it difficult to form a coating that is both biocompatible and that has drug-releasing properties.

In addition, treatments that are used to form coatings can in some cases damage the bioactive agent and therefore reduce the overall effectiveness of the coated article. This may be the case when irradiation is used to form all or part of the coating. Irradiation sources can be useful for activating components of a coating composition to form the coating, but can also lack the specificity and therefore cause degradation of the bioactive agent that is present in the coating.

Another problem relates to the release of bioactive agent, as some materials release the bioactive agent immediately upon contact with tissue; therefore the bioactive agent is not present for an amount of time sufficient to provide a beneficial effect.

SUMMARY OF THE INVENTION

The invention relates to methods and systems for providing biocompatible surfaces to medical devices. According to the invention, a biocompatible agent is coupled to the polymeric material to provide a biocompatible surface of the medical article.

In one aspect, the invention provides methods of coupling a biocompatible agent to a surface of a medical article, the methods including the following steps: (a) providing a polymeric material on a surface of a medical article, the polymeric material comprising one or more bioactive agents; and (b) providing biocompatible agent to the polymeric material under conditions sufficient to couple the biocompatible agent to the polymeric material, wherein coupling of the biocompatible agent with the polymeric material is accomplished by activating photoreactive groups provided by the polymeric material, the biocompatible agent, or both the polymeric material and the biocompatible material.

Optionally, the biocompatible agent can be premixed with a second polymeric material prior to application of the biocompatible agent to the polymeric material. The second polymeric material can be the same or different from the polymeric material provided on the surface of the medical article. That is, the biocompatible agent can be premixed with and coupled to a polymeric material prior to application on the surface.

In some embodiments, the biocompatible agent includes one or more photoreactive groups, and coupling of the biocompatible agent to the polymeric material is accomplished by activating one or more of the photoreactive groups of the biocompatible agent. That is, for example, the biocompatible agent having photoreactive groups is premixed and coupled to the polymeric material via the photoreactive groups prior to application on the surface.

In other aspects of the invention, the polymeric material includes one or more photoreactive groups, and coupling of the biocompatible agent to the polymeric material is accomplished by activating one or more of the photoreactive groups of the polymeric material. That is, for example, a polymeric material having photoreactive groups is premixed and coupled to the biocompatible agent via the photoreactive groups prior to application.

A composition that includes the polymeric material, biocompatible agent, and photoreactive groups can be utilized in a coating in a number of different ways. In some aspects, this composition is disposed over a bioactive-agent containing coated layer. In other aspects a bioactive agent is mixed into the composition and disposed on the surface of a device. In yet other aspects the composition can be disposed on an article to form a coating that does not include a bioactive agent. In any of these aspects the composition can be pre-treated to activate the photoreactive groups to couple the biocompatible agent to the polymeric material, before the composition is disposed.

In one aspect, the invention provides methods of providing a biocompatible coating to a surface of a medical article. The methods comprise the steps of (a) providing a coating composition comprising (i) a polymeric material, (ii) a biocompatible agent, and (iii) a photoreactive moiety, wherein the photoreactive moiety is pendent from (i), pendent from (ii), independent, or combinations thereof; (b) disposing the coating composition on the surface of the medical article; and (c) treating the coating composition to activate the photoreactive moiety. The photoreactive moiety can be activated to couple the polymeric material to the biocompatible agent. In some aspects it is preferable that the photoreactive moiety is pendent from the biocompatible agent.

In many aspects of the invention the step of treating the coating composition to activate the photoreactive moiety is performed before the step of disposing the coating composition on the surface of the medical article. In other aspects, the photoreactive moiety can be activated after or during the step of disposing. In yet other aspects activation of photoreactive moieties can be performed more than one time during the method. For example, the coating composition can be treated with UV irradiation before the step of disposing and after the composition is coated onto the surface. If a step of treating is performed more than one time it is preferred that there are photoreactive moieties capable of being activated present in the coating composition after the composition has been treated.

The polymeric material of the biocompatible coating composition preferably includes a polymer that has good adhesive properties (for example, a polymer that is "sticky"). This type of polymer, herein referred to as an "adherent polymer", can, in some embodiments, be deposited and stick to a surface without providing substantial additional treatment to make the polymer adhere. Many polymers having adherent properties are known in the art. Such a polymer with adherent properties can be synthetic or natural. Suitable polymers and copolymers include acrylate, methacrylate, ethylene glycol, vinyl pyrrolidinone, and glucose-monomeric units.

In some aspects the adherent polymer preferably includes poly(alkyl(meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

In yet other aspects the polymeric material is biodegradable. Suitable biodegradable polymers include, for example, polylactic acid and polyglycolic acid.

In some aspects, the polymeric material of the biocompatible coating composition is able to incorporate and controllably release or present a bioactive agent. The property of being able to incorporate and controllably release a bioactive agent can be provided by one or more polymers, or can be provided by a mixture of polymers. For example a mixture of an adherent polymer and a polymer that is different than that adherent polymer can be used. For example, in some preferred aspects, the coating composition has a mixture of polymers including poly(butyl)methacrylate and poly(ethylene-co-vinyl acetate).

In other aspects, the polymeric material of the coating composition includes polymers such as Parylene™ and ethylene vinyl alcohol.

In some aspects the biocompatible agent provides a hemocompatible (blood compatible) surface to the medical article. For example, a medical article with a hemocompatible coating can reduce effects that may associated with placing a foreign object in contact with blood components, such as the formation of thrombus or emboli (blood clots that release and travel downstream.

The biocompatible agent can be a larger molecule, such as a polymer that includes amino acid or saccharide monomeric units; or a smaller molecule that is non-polymeric, for example, a small synthetically prepared or naturally derived molecule.

In some aspects the biocompatible agent is a polymer, for example, a hydrophilic polymer having biocompatible properties (herein referred to as a "hydrophilic biocompatible polymer"). Preferably, the hydrophilic polymer has hemocompatible properties, meaning that it promotes compatibility with blood components by minimizing events that may compromise the function of the device, such as thrombus formation near the coated surface.

A hydrophilic biocompatible polymer can be a natural polymer, or can be derived from a natural polymer. The hydrophilic biocompatible polymer can also include charged groups, such as sulfonate groups. In some aspects the hydrophilic polymer is a polysaccharide. According to the invention, particularly useful polysaccharides can be selected from mucopolysaccharides such as heparin, hyaluronic acid, chondroitin, keratan, and dermatan. In preferred embodiments the biocompatible polymer is heparin. In some preferred embodiments, the biocompatible polymer is selected from heparin, heparin derivatives, sodium heparin, and low molecular weight heparin. As used herein "heparin" is meant to encompass all forms of heparin, including derivatives and different molecular weight preparations of heparin.

It has been discovered that a bioactive agent releasing coating that has excellent heparin activity can be formed according to the inventive methods described herein. In determining the heparin activity, an assay can be performed and compared to results of an assay performed using heparin standards.

Therefore, in some aspects, the invention provides a medical article having a bioactive agent-releasing coating having heparin activity of 10 mU/cm$^2$ or greater. Bioactive agent-releasing coatings were also prepared having a heparin activity of 15 mU/cm$^2$ or greater, 20 mU/cm$^2$ or greater, 25 mU/cm or greater, 30 mU/cm$^2$ or greater, 35 mU/cm or greater, 40 mU/cm$^2$ or greater, 45 mU/cm$^2$ or greater, and 50 mU/cm$^2$ or greater. Biocompatible coatings having these activities can also be formed without a bioactive agent being present in the coating.

In one aspect, the photoreactive moiety present in the coating composition is pendent from the biocompatible agent. One example of a biocompatible agent having a pendent photoreactive moiety is photo-heparin, as described herein. Another example is photocollagen, as described herein. The pendent photoreactive moiety is activatable, meaning that it can be activated to form a radical species that can extract hydrogen from a target moiety, and thereby form a covalent bond between, for example, the biocompatible agent and a target moiety. For example, the photoreactive group can be activated to couple the biocompatible agent to the polymeric material.

The invention also provides a coating compound formed by treating a coating composition that comprises an adherent polymer and a biocompatible agent, wherein the adherent polymer and the biocompatible agent are coupled via a photoreactive moiety. In one particular aspect, the invention provides poly(butyl)methacrylate-heparin and/or poly(butyl)methacrylate-collagen adducts, wherein the poly(butyl)methacrylate is coupled to the heparin or the collagen via a photoreactive moiety.

In another aspect, the polymeric material can be coupled to the biocompatible agent using a bifunctional reagent, that includes a photoreactive group, and another latent reactive group, such as a thermally reactive group. In this aspect, the latent reactive group is reactive with a portion of the biocompatible agent, and the photoreactive group is reactive with the polymeric material. Suitable thermally reactive groups include NOS groups (N-oxysuccinimide). An exemplary method of coupling involves reacting a NOS groups of a bifunctional reagent with an amine group of heparin, and activating the photoreactive group to bind a polymeric material such as poly(butyl(meth)acrylate).

In another aspect of the invention, a miscibility enhancer is added to the biocompatible coating composition. A miscibility enhancer can be used to improve the homogeneity of the polymeric material and the biocompatible agent in the coating composition and improve the overall coating composition. According to the invention, the miscibility enhancer can be used improve the coupling of the biocompatible agent to the polymer, for example, an adherent polymer.

The miscibility enhancer can be a compound that can improve the compatibility of the adherent polymer with the biocompatible agent. For example, in some aspects the adherent polymer is hydrophobic, while the biocompatible agent is hydrophilic. In some cases, for example, an amphoteric agent can be used as the miscibility enhancer.

The miscibility enhancer can be selected from the group consisting of polyvinylpyrrolidinone (PVP), polyethyleneglycol (PEG), PEG sulfonates, fatty quaternary amines, fatty sulfonates, fatty acids, dextran, dextrin, and cyclodextrin. The miscibility enhancer can also include pendant photoreactive groups.

Therefore, in another aspect, the invention provides another method for providing a biocompatible surface of a medical device. The method comprises the steps of (a) providing a coating composition comprising (i) an adherent polymer, (ii) miscibility enhancer, (iii) a biocompatible agent, and (iv) a photoreactive moiety, and wherein the photoreactive moiety is pendent from (i), pendent from (ii), pendent from (iii), independent, or combinations thereof; (b) disposing the coating composition on the surface of the medical article; and (c) treating the coating composition to activate the photoreactive group.

In some aspects the biocompatible layer includes at least three components and photoreactive groups. In some aspects the biocompatible layer includes at least three polymers. One of the three polymers can be a hydrophobic polymer (such as a poly(alkyl(meth)acrylate), another is a biocompatible polymer (such as heparin), and the other is a poly(vinylpyrrolidone) polymer. In the biocompatible coated layer, the photoreactive groups have been activated either prior to the coating composition being deposited on the article, after the coating composition has been deposited on the article, or both before and after the coating composition has been deposited on the article.

In a preferred aspect the biocompatible coated layer consists of (i) a hydrophobic polymer, preferably a poly(alkyl(meth)acrylate) such as pBMA, present in the layer in an amount by weight in the range of 75% to 90%; (ii) hydrophilic biocompatible polymer such as heparin present in the layer in an amount by weight in the range of 5% to 15%; and (iii) a PVP polymer present in the layer in an amount by weight in the range of 5% to 15%.

In some embodiments, the photoreactive moiety is pendent from the biocompatible agent. Upon activation of the photoreactive groups the biocompatible agent can be coupled to another component, for example, the polymeric material. The coupling can be performed in one step, for example prior to disposing the composition on the medical article, or in more than one step, for example, before and after (and/or during) the step of disposing.

In yet other embodiments the photoreactive moiety is independent of the biocompatible agent and the polymeric material. For example, the photoreactive moiety is a molecule having at least one photoreactive group that is able to couple the biocompatible agent to the polymeric material when activated. One example is a crosslinking agent that includes two or more photoreactive groups.

In some cases the method of providing a biocompatible coating to a surface of a medical article includes a step of providing a medical article having a bioactive agent-releasing layer. While, in some cases, a medical article having a bioactive agent-releasing layer can be obtained, in other cases the method can include a step of forming a bioactive agent-releasing layer on the surface of a medical article.

The bioactive agent can be released from or presented by the coating once the coating is formed on the medical article and implanted in a patient. In some embodiments, the coating composition can include more than one bioactive agent, wherein each of the bioactive agents can be independently selected depending upon the desired therapeutic application of the invention.

Accordingly, the invention also provides a medical article having a biocompatible, bioactive agent releasing coating, the coating comprising a bioactive agent-releasing layer and a biocompatible layer. The term "bioactive agent-releasing layer" refers to the coated layer that is prepared from a coating composition that includes a bioactive agent intended to be released from the coating. It is understood that when the coating is formed, and/or after the coating is formed, the bioactive agent can become present in layers other than the bioactive agent-releasing layer. The bioactive agent-releasing layer is formed between biocompatible layer (i.e., the coated layer that includes the biocompatible agent) and the surface of the article. The bioactive agent-releasing layer can also include a polymeric material, such as a hydrophobic polymer. As indicated, the composition that includes the biocompatible agent, polymeric material, and the photoreactive groups can be irradiated prior to disposing the composition on the bioactive-agent releasing layer.

The coated medical article can function to release a bioactive agent in a localized and controlled manner from the surface of the article, when the article is placed in vivo, such as by implantation or delivery to a target region in the body. To be released in a localized and controlled manner, the bioactive agent, initially being present in the bioactive agent-releasing layer, can pass through the biocompatible layer before the bioactive agent is released in a localized manner. Optionally, the bioactive agent can pass through any other coated layer that is between the bioactive agent-containing layer and the outermost layer (i.e., the layer that is in contact with a physiological environment) of the coated article that may be present in the coating. The bioactive agent then becomes locally therapeutically available when it reaches the interface of the coating and body tissue or fluid.

Therefore, in some aspects of the invention, a method for preparing a medical article having a bioactive agent-releasing coating with heparin activity can include the steps of providing a medical article having a first coated layer comprising a bioactive agent; irradiating a composition comprising heparin, photoreactive groups, and polymeric material to activate the photoreactive groups; and then after the irradiation step, disposing the irradiated composition on the first coated layer.

In some aspects the bioactive agent-releasing layer can include a hydrophobic polymer selected from the group consisting of poly(meth)acrylates. In a preferred aspect the bioactive agent-releasing layer includes a poly(alkyl(meth)acrylates) having a short chain alkyl group, such as those in the range of $C_2$-$C_5$, including propyl ($C_3$), and most preferably butyl ($C_4$). Most preferably the bioactive agent-releasing layer includes poly(butyl(meth)acrylate) (pBMA).

In another aspect the bioactive agent-releasing layer includes a first polymer which is hydrophobic and a second polymer that is different than the first polymer. The second polymer can be a polymer that improves or changes one or more properties of the bioactive agent-releasing layer. For example a second polymer can improve the pliability of the first layer, or can change the characteristics of the release of the bioactive agent from the bioactive agent-releasing layer. Second polymers can include polymers having ethylene and vinyl acetate monomeric units, and preferably ethylene and vinyl acetate copolymers (poly(ethylene-co-vinyl acetate); pEVA). In some preferred embodiments, the bioactive agent-releasing layer includes a blend of pBMA and pEVA polymers.

The invention also contemplates medical articles having a biocompatible coating that does not include a bioactive agent-releasing layer. Because the inventive biocompatible coating compositions described herein have outstanding utility, coatings can be formed wherein drug release is not a required feature, although biocompatibility is. Therefore, in some aspects, the invention provides a medical article having a biocompatible coated layer, and optionally other layers that do not include a bioactive agent.

According to the invention, at least a portion of the surface of the medical article is coated with the coating composition. In some embodiments, the entire surface of the medical article can be coated with the coating composition. The amount of the surface area provided with the polymeric material can be determined according to such factors as the medical device to be utilized, the application of the device, the bioactive agent to be utilized with the polymeric material, and the like factors.

The coating composition described herein can be deposited on the medical article utilizing any known application technique. In some preferred aspects, the coating composition is applied by spray coating. In other aspects, the coating composition is deposited on the medical article by dip coating the medical article in the coating composition. The coating composition can be treated before, after, or before and after the coating is deposited on the medical article.

In other aspects, the invention provides a medical article having a coating ("a coated composition"), the coating comprising a polymeric material, a biocompatible agent, and a photoreactive and/or photoreacted moiety. In preferred aspects the components of the coating composition are deposited on the surface in a single application of coating material. The photoreactive moiety can couple the biocompatible agent to at least the polymeric material. The coating includes a layer wherein both the polymeric material and the biocompatible agent are present, that is, the coating includes a layer of material wherein the biocompatible agent is dispersed in and/or coupled to the polymeric material via the photoreactive moiety. Advantageously, after the coating composition has been disposed on the surface of the medical article, the biocompatible agent is arranged in the coated composition in such a manner as to provide excellent biocompatible surface properties.

The invention generally relates to methods and systems for providing a biocompatible coating to a medical article. In some aspects, the invention relates to forming a biocompatible coating on a medical article, the medical article having another coated layer that includes and than can release a bioactive agent. According to the invention, the biocompatible layer in conjunction with the bioactive agent-releasing layer form a coating that has excellent biocompatibility and bioactive agent-releasing properties.

According to the invention, the biocompatible coating can be formed using an improved coating composition that includes polymeric components and photoreactive moieties. Some of the compositions described herein include heparin and can be used to form coatings that have heparin activity. For example, the methods and compositions are used to provide a biocompatible coated layer having heparin activity to a medical article having a formed bioactive agent-releasing coated layer.

The biocompatible layer improves the function of the medical article in many ways. For example, the biocompatible layer can substantially reduce the accumulation of clotting components on the surface of the article. This reduction means that the release of the bioactive agent will not be compromised by any sort of blockage on the surface of the device as caused by the clotting components. In addition, the biocompatible coated layer can also improve the mechanical function of the device, as these similar components will not accumulate on the device and compromise its mechanical function. In this manner, the coating has excellent anti-adherence properties. These anti-adherence properties are thought, at least in part, to be provided by the combination of the polymeric materials in the biocompatible layer (for example, the hydrophilic biocompatible polymer and the PVP polymer).

The composition and methods of the invention can provide one or more distinct advantages for the preparation of biocompatible, bioactive agent-releasing medical articles. While the preparation of a surface of a medical article that has both drug-releasing and biocompatible properties can be challenging from a number or perspectives, the invention provides a way to prepare these types of coated surfaces without compromising properties that are provided by the individual components and which can be important for in vivo use. Illustrative advantages that can be observed with the inventive compositions and methods will now be discussed. It is understood that any one or more of these may be demonstrated by the invention.

One advantage relates to the ability to efficiently and cost effectively provide a coated layer having biocompatibility to a medical article, the medical article also having a bioactive agent-releasing coated layer. This can be seen, in some aspects, by the ability to form a bioactive agent-releasing, biocompatible coating on the surface of a medical article in minimal number of steps. In some cases, and in its simplest form, a coating can be formed by applying the biocompatible coating composition onto a medical article having one, or more then one, pre-formed coated layer(s) that includes a bioactive agent. In other cases, the coating can be formed in a method that includes two steps, that is, a coating is formed by disposing a first composition that includes a bioactive agent, and subsequently a second composition that includes a biocompatible polymer. The methods described herein greatly reduce the throughput time for the fabrication of medical articles having biocompatible and bioactive agent-releasing properties. This, in turn, can result in a substantial cost savings for the preparation of these medical articles, as many reagents and steps that might typically be attempted in fabrication of these coated medical articles are not necessarily required.

Another advantage of the present invention is that a biocompatible coating can be formed on the surface of a bioactive agent-releasing layer without significantly compromising the bioactive agent-releasing properties of the coating. For example, a coating with heparin activity can be formed on a medical article having a drug-releasing layer without significantly altering the drug releasing profile of the coating. Also, according to the invention, the presence of a bioactive agent-releasing layer does not compromise the formation or properties of a coated layer having biocompatible properties, such as heparin activity. Such results are seen because the present invention overcomes typical problems that can be encountered when multiple layers of coated materials are provided to a surface in order to provide a coating having more than one property. Therefore, in this regard, the properties of the inventive coatings described herein with regard to biocompatibility (e.g., heparin activity) and bioactive agent release are particularly surprising, as one would not expect that the biocompatible and drug-releasing properties would be maintained at levels that were achieved by preparation of these coatings not in combination. In other words, while it was expected that the combination of coated layers would lead to a decrease in the activity of each layer, this expectation, in fact, was not realized based on the results seen when bioactivity and drug release were tested on the inventive coatings described herein.

Yet another advantage of preferred embodiments of the invention is that it can provide methods for the preparation of biocompatible coating compositions that include polymeric materials which are typically difficult to combine and/or do not form a coated layer that has suitable activity or physical properties. Accordingly, the invention also provides methods for forming a coated layer on the surface of a medical article that includes combinations of these types of polymeric materials. The present invention overcomes problems, specifically, with preparing a coating composition that includes a hydrophilic biocompatible polymer and a hydrophobic polymeric material. The present invention not only overcomes challenges posed with the preparation of these coating compositions, but also challenges associated with forming a coating on the surface of an article, wherein the polymeric components are well dispersed (or mixed) in the coating and have properties that are reflected by the presence of both the hydrophilic biocompatible polymer and a hydrophobic polymeric material.

Yet another advantage of preferred embodiments of the invention is seen from results showing that the biocompatible bioactive-agent releasing coating has excellent durability. Test results demonstrate that the coating is durable and retains good biocompatible properties after the article has been subject to physical stresses. Such physical stresses may otherwise cause inferior (unacceptable) coatings to crack or delaminate from the surface of the device, thereby compromising the function of the coating by reducing, for example, biocompatible activity. Physical stresses can be encountered at one or more points during processes involving use of the article, including insertion of the article into the body.

Excellent biocompatible properties were also observed after the coated article was placed in a biochemical environment simulating the biochemical stresses that are encountered when the coated article is placed in vivo. It is generally desirable to form coatings that not degrade and that are not fouled by the presence of body fluids such as blood. Rather, it is desirable that the coatings display prolonged biocompatible activity in conjunction with the function of the device. Results of analysis of the inventive coatings described herein demonstrate that the coated articles are resistant to losing biocompatible properties even after the coated articles have been placed in conditions that simulate a physiological environment for an extended period of time.

Still yet another advantage of the invention is the ability to pre-treat components that are associated with the biocompatible coated layer, prior to disposing the biocompatible coating composition on an article having a bioactive agent coated layer. "Pre-treating" refers to applying a source of energy, such as actinic radiation (e.g., UV irradiation), that activates the photoreactive groups that are present in the biocompatible coating composition. These photoreactive groups are activated as a step in the process of forming the biocompatible layer, and generally serve to couple the polymeric agents that are present in this composition. While the step of applying a source of energy to the biocompatible composition can be performed before or after the composition is coated on the article, in many instances it is desirable to perform this step prior to disposing the composition. For example, a clear benefit of pre-treatment would be avoiding irradiating the article having a bioactive coated layer that includes a bioactive agent that is sensitive and, for example, can become inactive (for example, by degradation), upon exposure to this irradiation. Advantageously, the biocompatible coating composition that was pre-treated and disposed on an article having a bioactive agent-containing layer was able to form a layer having excellent biocompatible properties and that also provided an overall coating that demonstrated excellent bioactive agent release profiles. Therefore, this pre-treatment method preserves the quality of bioactive agents.

The invention will now be described in more detail.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

The present invention is directed to methods for preparing a biocompatible surface on a medical article. The biocompatible surface thus enhances the ability of the medical article to function or exist in contact with biological fluid and/or tissue of a living organism with a net beneficial effect on the living organism. In preferred embodiments, the biocompatible surface can provide one or more advantages, such as increased patient safety, improved device performance, reduced adherence of unwanted blood components, inhibition of blood clotting, maintenance of device surfaces free of cellular debris, and/or extension of the useable lifetime of the device.

The methods described herein are particularly suitable for preparing a biocompatible surface on a medical article. In one embodiment, the biocompatible surface can be prepared by disposing a coating composition that includes a polymeric material, a biocompatible agent, and a photoreactive moiety on a substrate. In preferred embodiments the photoreactive moiety is pendent from the biocompatible agent. In another embodiment, a biocompatible surface can be prepared by disposing a coating composition that includes a polymeric material, a biocompatible agent, a miscibility enhancer, and a photoreactive moiety. The polymeric material preferably includes an adherent polymer that is capable of adhering to a surface.

A bioactive agent can also be included in the coating composition. The presence of one or more bioactive agents in a coating that is on the surface of the medical article may render the device surface sensitive to irradiation with light, since certain wavelengths can inactivate bioactive agents.

In some aspects, the invention provides a multi-component coating formed on the surface of a medical article has properties including being (i) bioactive-agent releasing and (ii) biocompatible. Generally, the coating includes at least two coated layers, (i) one layer being a bioactive agent-releasing layer that includes a polymeric material having a bioactive agent, and (ii) another layer being a biocompatible layer that includes two or more polymeric materials (one of them being a biocompatible polymer) and photoreactive groups. The bioactive agent-releasing layer is formed between the biocompatible layer and the surface of the article. The coating can consist of these two layers, or can optionally include other layers.

In forming the biocompatible coating, the coating composition that includes the biocompatible polymer and photoreactive groups is irradiated. The coating composition can be irradiated to activate the photoreactive groups before or after the coating composition is disposed on the surface, or both before and after. The exact method of irradiation may depend on the type and/or amount of photoreactive group that is associated with the coating on the surface of the article.

In some embodiments, the photoreactive moiety is pendent from the biocompatible polymer. For example, at least one photoreactive group is covalently bonded to the biocompatible polymer. Upon activation of the photoreactive groups the biocompatible polymer can be coupled to another component, for example, the polymeric material. The coupling can be performed in one step, for example prior to disposing the composition on the medical article, or in more than one step, for example, before and after (and/or during) the step of disposing. In some embodiments, a filter is utilized in connection with the step treating, which can involve the activation of the one or more photoreactive groups. In embodiments wherein a bioactive agent is included in the coating composition, the one or more photoreactive groups are activated by providing light having a wavelength selected in a range to activate the photoreactive groups and minimize inactivation of bioactive agent in the polymeric material.

The methods described herein are also particularly suitable for preparing a biocompatible, bioactive agent-releasing coating on a medical article. In some preferred aspects the biocompatible coating composition is disposed on a medical article having a bioactive agent-releasing layer. The bioactive agent releasing layer can include a bioactive agent and a hydrophobic polymer, for example a poly(alkyl(meth)acrylate) such as pBMA.

The invention also relates to methods for providing a biocompatible surface to an implantable medical article. The implantable medical article can be, for example, a stent or a synthetic graft having a structure adapted for the introduction into a patient. In some embodiments the device is coated with coating composition that includes a polymeric material and one or more bioactive agents for delivery of a drug or pharmaceutical substance to tissues adjacent the site of implantation. In some cases reference is made to a stent having a drug-containing polymeric matrix on its surface (also referred to as a drug-eluting stent, or "DES") and having a biocompatible surface. The methods and compositions of the invention in connection with DES have been chosen because these devices are designed to reside in the body for extended periods of time, thus increasing risk of adverse body reactions to the device. Further, in terms of lowering the risk while providing a superior device, the advantages of this invention can be clearly presented. However, it is understood that the methods disclosed are applicable to any medical articles where attachment of a biocompatible agent are desirable, and are not limited to the particular medical article surfaces described herein.

In some embodiments, the invention provides methods of providing biocompatible surfaces to medical devices that carry a polymeric material that can have bioactive agents associated therewith. The invention can be utilized in connection with medical devices having a variety of biomaterial surfaces. Preferred biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, and vinylidene difluoride. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketone.

Certain natural materials are also suitable biomaterials, including human tissue such as bone, cartilage, skin and teeth; and other organic materials such as wood, cellulose, compressed carbon, and rubber. Other suitable biomaterials include metals and ceramics. The metals include, but are not limited to, titanium, Nitinol, stainless steel, tantalum, and cobalt chromium. A second class of metals includes the noble metals such as gold, silver, copper, and platinum uridium. Alloys of metals are suitable for biomaterials as well. The ceramics include, but are not limited to, silicon nitride, silicon carbide, zirconia, and alumina, as well as glass, silica, and sapphire.

Combinations of ceramics and metals are another class of biomaterials. Another class of biomaterials is fibrous or porous in nature. The surface of such biomaterials can be pretreated (for example, with a Parylene™-containing coating composition) in order to alter the surface properties of the biomaterial, when desired.

Biomaterials can be used to fabricate a variety of implantable devices. The medical device can be any device that is introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

Compositions of this invention can be used to coat the surface of a variety of implantable devices, for example: drug-delivering vascular stents; other vascular devices (e.g., grafts, catheters, valves, artificial hearts, heart assist devices); implantable defibrillators; blood oxygenator devices; surgical devices; tissue-related materials; membranes; cell culture devices; chromatographic support materials; biosensors; shunts for hydrocephalus; wound management devices; endoscopic devices; infection control devices; orthopedic devices; dental devices, urological devices; colostomy bag attachment devices; ophthalmic devices; glaucoma drain shunts; synthetic prostheses; intraocular lenses; respiratory, peripheral cardiovascular, spinal, neurological, dental, ear/nose/throat (e.g., ear drainage tubes); renal devices; and dialysis (e.g., tubing, membranes, grafts).

Examples of useful devices include self-expanding stents (e.g., made from nitinol), balloon-expanded stents (e.g., prepared from stainless steel), degradable coronary stents, non-degradable coronary stents, peripheral coronary stents, urinary catheters (e.g., surface-coated with antimicrobial agents), penile implants, sphincter devices, urethral devices, bladder devices, renal devices, vascular implants and grafts, intravenous catheters (e.g., treated with antithrombotic agents), small diameter grafts, artificial lung catheters, electrophysiology catheters, anastomosis devices, vertebral disks, bone pins, suture anchors, hemostatic barriers, clamps, surgical staples/sutures/screws/plates/clips, atrial septal defect closures, electro-stimulation leads for cardiac rhythm management (e.g., pacer leads), glucose sensors (long-term and short-term), blood pressure and stent graft catheters, blood oxygenator tubing, blood oxygenator membranes, blood bags, birth control devices, breast implants, ); benign prostatic hyperplasia and prostate cancer implants, bone repair/augmentation devices, breast implants, cartilage repair devices, orthopedic joint implants, orthopedic fracture repairs, tissue adhesives, tissue sealants, tissue scaffolds, CSF shunts, dental implants, dental fracture repair devices, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, central venous access catheters, hemodialysis devices, catheter cuff, anastomotic closures, vascular access catheters, cardiac sensors, uterine bleeding patches, urological catheters/stents/implants, in vitro diagnostics, aneurysm exclusion devices, neuropatches, Vena cava filters, urinary dialators, endoscopic surgical tissue extractors, atherectomy catheters, clot extraction catheters, PTA catheters, PTCA catheters, stylets (vascular and non-vascular), coronary guidewires, drug infusion catheters, esophageal stents, circulatory support systems, angiographic catheters, transition sheaths and dialators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

The methods and compositions described herein are particularly useful for those devices that will come in contact with aqueous systems, such as bodily fluids. Such devices can be coated with a coating composition adapted to release bioactive agent in a prolonged and controlled manner, generally beginning with the initial contact between the device surface and its aqueous environment. It is important to note that the local delivery of combinations of bioactive agents may be utilized to treat a wide variety of conditions utilizing any number of medical devices, or to enhance the function and/or life of the device. Essentially, any type of medical device may be coated in some fashion with one or more bioactive agents that enhances treatment over use of the singular use of the device or bioactive agent.

According to the invention, the biocompatible agent is utilized to provide a biocompatible surface to a medical device. The solid surface that is rendered biocompatible is desirably of a synthetic or natural material that is insoluble, at least initially, in physiological fluids. The surface can be one or more surfaces of devices intended to function in contact with tissue and/or fluids of living organisms.

According to the invention, the coating composition includes a polymeric material disposed or provided on the surface of a medical article. The polymers can be bio-stable or biodegradable, organic or inorganic, and synthetic or naturally occurring substances. The polymeric material can be selected from a variety of polymeric materials. Preferably, the polymeric material has adherent properties, meaning that it can be deposited on and stick to a surface.

In some aspects, the coating composition can be disposed on the medical article having a surface that has been primed to facilitate adherence of the coating composition onto the medical article.

As used herein, "polymeric material" refers to homopolymers, copolymers, and combinations and mixtures thereof.

According to the invention, the polymeric material can be used in the biocompatible coating composition or coated layer that includes the biocompatible agent, in a bioactive active agent-containing layer or composition used to form this layer, or in another coated layer or composition, or combinations thereof.

In some embodiments, the coating composition includes a polymeric material that is selected to incorporate a desirable amount of the bioactive agent, and to either retain the bioactive agent so that it is sufficiently presented to the surrounding physiological environment, or to release the bioactive agent to provide a desired elution profile.

Any suitable bio-stable or biodegradable polymeric materials can be used.

Bio-stable polymeric materials include, but are not limited to, polymers of polyurethanes, polyethylenes, polyethylene teraphthalates, ethylene vinyl acetates, silicones and polyethylene oxide. Ethylene vinyl alcohol copolymers can also be used. Some preferred polymeric materials include mixtures of poly(butylmethacrylate) and poly(ethylene-co-vinyl acetate), and Parylene™. Bio-stable polymers can be permeable to the bioactive agent, which can be released by diffusion through and out of the polymeric material.

In some aspects, the invention provides a biocompatible, bioactive agent-releasing coating that includes at least two layers, a bioactive agent-releasing layer and a biocompatible layer. Both of these layers can include a hydrophobic polymer. In some preferred aspects of the invention, these layers include the same hydrophobic polymer. The hydrophobic polymer is preferably a poly(alkyl(meth)acrylate), where "(meth)" will be understood by those skilled in the art to include such molecules in either the acrylic and/or methacrylic form (corresponding to the acrylates and/or methacrylates, respectively).

In one embodiment, the polymeric material comprises a composition as described in U.S. Pat. No. 6,214,901 (Chudzik et al.) and U.S. Publication No.2002/0188037 A1 (Chudzik et al.) (each commonly assigned to the assignee of the present invention). As described therein, the composition comprises a plurality of polymers, including at least two polymer components, for example, primary and secondary polymer components. As used herein "primary" and "secondary" are used solely for designation of the polymer components are not intended to reflect the relative amounts of polymer components in the composition. The polymer components are adapted to be mixed to provide a mixture that exhibits an optimal combination of physical characteristics (such as adherence, durability, flexibility) and bioactive release characteristics as compared to the polymers when used alone or in admixture with other polymers previously known. For example the polymeric material can include an adherent polymer and a polymer having drug release characteristics.

In some aspects the adherent polymer preferably includes poly(alkyl(meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

Examples of suitable poly(alkyl (meth)acrylates) include those with alkyl chain lengths from 2 to 8 carbons, inclusive, and with molecular weights from 50 kilodaltons to 900 kilodaltons. In one preferred embodiment the polymeric material includes a poly(alkyl (meth)acrylate) with a molecular weight of from about 100 kilodaltons to about 1000 kilodaltons, preferably from about 150 kilodaltons to about 500 kilodaltons, most preferably from about 200 kilodaltons to about 400 kilodaltons. An example of a particularly preferred polymer is poly (n-butyl methacrylate). Examples of other preferred polymers are poly(n-butyl methacrylate-co-methyl methacrylate, with a monomer ratio of 3:1, poly(n-butyl methacrylate-co-isobutyl methacrylate, with a monomer ratio of 1:1 and poly(t-butyl methacrylate). Such polymers are available commercially (e.g., from Sigma-Aldrich, Milwaukee, Wis.) with molecular weights ranging from about 150 kilodaltons to about 350 kilodaltons, and with varying inherent viscosities, solubilities and forms (e.g., as slabs, granules, beads, crystals or powder).

Examples of suitable poly(aromatic(meth)acrylates) include poly(aryl(meth)acrylates), poly(aralkyl(meth)acrylates), poly(alkaryl(meth)acrylates), poly(aryloxyalkyl (meth)acrylates), and poly(alkoxyaryl(meth)acrylates).

Examples of suitable poly(aryl (meth)acrylates) include poly(9-anthracenyl methacrylate), poly(chlorophenyl acrylate), poly(methacryloxy-2-hydroxybenzophenone), poly (methacryloxybenzotriazole), poly(naphthyl acrylate), poly (naphthylmethacrylate), poly-4-nitrophenylacrylate, poly (pentachloro(bromo, fluoro) acrylate) and methacrylate, poly (phenyl acrylate) and poly(phenyl methacrylate). Examples of suitable poly(aralkyl(meth)acrylates) include poly(benzyl acrylate), poly(benzyl methacrylate), poly(2-phenethyl acrylate), poly(2-phenethyl methacrylate) and poly(1-pyrenylmethyl methacrylate). Examples of suitable poly(alkaryl(meth) acrylates include poly(4-sec-butylphenyl methacrylate), poly (3-ethylphenyl acrylate), and poly(2-methyl-1-naphthyl methacrylate). Examples of suitable poly(aryloxyalkyl (meth)acrylates) include poly(phenoxyethyl acrylate), poly (phenoxyethyl methacrylate), and poly(polyethylene glycol phenyl ether acrylate) and poly(polyethylene glycol phenyl ether methacrylate) with varying polyethylene glycol molecular weights. Examples of suitable poly(alkoxyaryl (meth)acrylates) include poly(4-methoxyphenyl methacrylate), poly(2-ethoxyphenyl acrylate) and poly(2-methoxynaphthyl acrylate).

Acrylate or methacrylate monomers or polymers and/or their parent alcohols are commercially available from Sigma-Aldrich (Milwaukee, Wis.) or from Polysciences, Inc, (Warrington, Pa.).

One of the other polymer components in the mixture provides an optimal combination of similar properties, and particularly when used in admixture with the primary polymer component. Examples of suitable secondary polymers are available commercially and include poly(ethylene-co-vinyl acetate) having vinyl acetate concentrations in the range of about 1% to about 50%, in the form of beads, pellets, granules, and the like.

In some embodiments, the composition comprises at least one poly(alkyl)(meth)acrylate, as a primary, adherent polymeric component, and poly(ethylene-co-vinyl acetate) as a secondary polymeric component. Preferably, the polymer mixture includes mixtures of poly(butylmethacrylate) (PBMA) and poly(ethylene-co-vinyl acetate) (pEVA). This mixture of polymers has proven useful with absolute polymer concentrations (total combined concentrations of both polymers in the composition) in the range of about 0.25 to about 70% (by weight). It has furthermore proven effective with individual polymer concentrations in the coating solution in the range of about 0.05 to about 70% (by weight). In one preferred embodiment, the polymer mixture includes poly (n-butylmethacrylate) (PBMA) with a molecular weight in the range of about 100 kD to 900 kD and a pEVA copolymer with a vinyl acetate content in the range of about 24 to 36% (by weight). In another preferred embodiment, the polymer mixture includes poly (n-butylmethacrylate) (PBMA) with a molecular weight in the range of about 200 kD to 400 kD and a pEVA copolymer with a vinyl acetate content in the range of about 30 to 34% (by weight). According to these embodiments, the concentration of the bioactive agent or agents dissolved or suspended in the coating mixture can be in the range of about 0.01 to 90%, by weight, based on the weight of the final coating composition.

Other useful mixtures of polymers that can be included in the coating composition are described in commonly assigned U.S. Patent Application entitled, "COATING COMPOSITIONS FOR BIOACTIVE AGENTS,". These blends includes a first polymer and a second polymer. The first polymer can be selected from the group consisting of (i) poly (alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. A second polymer can be selected from the group consisting of poly(alkyl (meth)acrylates) and poly(aromatic (meth)acrylates).

Other useful mixtures of polymers that can be included in the coating are described in U.S. Publication No. 2004/0047911. This publication describes polymer blends that include poly(ethylene-co-methacrylate) and a polymer selected from the group consisting of a poly(vinyl alkylate), a poly(vinyl alkyl ether), a poly(vinyl acetal), a poly(alkyl and/or aryl methacrylate) or a poly(alkyl and/or aryl acrylate); not including pEVA.

The polymeric material can also be a styrene copolymer, such as poly(styrene-isobutylene-styrene); the preparation of medical devices having such coatings that include poly(styrene-isobutylene-styrene) is described in, for example, U.S. Pat. No. 6,669,980.

In some embodiments, the biocompatible, bioactive agent-releasing coating includes a tie layer. The tie layer can improve association of the bioactive agent-releasing layer with the article itself, and can include any sort of material which is compatible with the function of the article. Particularly useful materials include polymeric material, such as Parylene™ or a Parylene™ derivative.

In some embodiments, the polymeric material comprises Parylene™ or a Parylene™ derivative. "Parylene" is both a generic name for a known group of polymers based on p-xylylene and made by vapor phase polymerization, and a name for the unsubstituted form of the polymer; the latter usage is employed herein. More particularly, Parylene™ or a Parylene™ derivative is created by first heating p-xylylene or a suitable derivative at an appropriate temperature (for example, at about 100-150° C.) to produce the cyclic dimer di-p-xylylene (or a derivative thereof). The resultant solid can be separated in pure form, and then cracked and pyrolyzed at an appropriate temperature (for example, at about 690° C.) to produce a monomer vapor of p-xylylene (or derivative); the monomer vapor is cooled to a suitable temperature (for example, below 30° C.) and allowed to condense on the desired object, for example, on the surface of the medical device.

As indicated, Parylene™ and Parylene™ derivative coatings applicable by vapor deposition are known for a variety of biomedical uses, and are commercially available from or through a variety of sources, including Specialty Coating Systems (100 Deposition Drive, Clear Lake, Wis. 54005), Para Tech Coating, Inc. (35 Argonaut, Aliso Viejo, Calif. 92656) and Advanced Surface Technology, Inc. (9 Linnel Circle, Billerica, Mass. 01821-3902).

As used herein, biodegradable polymers are capable of being broken down by various enzymes, such as those in the normal functioning of the human body and living organisms (such as bacteria) and/or in water environments (simple hydrolysis). Once broken down, these polymers are gradually absorbed or eliminated by the body.

Examples of classes of synthetic polymers that have been studied as biodegradable materials include polyesters, polyamides, polyurethanes, polyorthoesters, polycaprolactone (PCL), polyiminocarbonates, aliphatic carbonates, polyphosphazenes, polyanhydrides, and copolymers thereof. Specific examples of biodegradable materials that can be used in connection with implantable medical devices include polylactide, polygylcolide, polydioxanone, poly(lactide-co-glycolide), poly(glycolide-co-polydioxanone), polyanhydrides, poly(glycolide-co-trimethylene carbonate), and poly(glycolide-co-caprolactone). Blends of these polymers with other biodegradable polymers can also be used. Typically, release of a bioactive agent occurs as these polymers dissolve or degrade in situ.

Biodegradable polyetherester copolymers can be used. Generally speaking, the polyetherester copolymers are amphiphilic block copolymers that include hydrophilic (for example, a polyalkylene glycol, such as polyethylene glycol) and hydrophobic blocks (for example, polyethylene terephthalate). Examples of block copolymers include poly(ethylene glycol)-based and poly(butylene terephthalate)-based blocks (PEG/PBT polymer). Examples of these types of multiblock copolymers are described in, for example, U.S. Pat. No. 5,980,948. PEG/PBT polymers are commercially available from Octoplus BV, under the trade designation PolyActive™.

Biodegradable copolymers having a biodegradable, segmented molecular architecture that includes at least two different ester linkages can also be used. The biodegradable polymers can be block copolymers (of the AB or ABA type) or segmented (also known as multiblock or random-block) copolymers of the $(AB)_n$ type. These copolymers are formed in a two (or more) stage ring opening copolymerization using two (or more) cyclic ester monomers that form linkages in the copolymer with greatly different susceptibilities to transesterification. Examples of these polymers are described in, for example, in U.S. Pat. No. 5,252,701 (Jarrett et al., "Segmented Absorbable Copolymer").

Other suitable biodegradable polymer materials include biodegradable terephthalate copolymers that include a phosphorus-containing linkage. Polymers having phosphoester linkages, called poly(phosphates), poly(phosphonates) and poly(phosphites), are known. See, for example, Penczek et al., Handbook of Polymer Synthesis, Chapter 17: "Phosphorus-Containing Polymers," 1077-1132 (Hans R. Kricheldorf ed., 1992), as well as U.S. Pat. Nos. 6,153,212, 6,485,737, 6,322,797, 6,600,010, 6,419,709. Biodegradable terephthalate polyesters can also be used that include a phosphoester linkage that is a phosphite. Suitable terephthalate polyester-polyphosphite copolymers are described, for example, in U.S. Pat. No. 6,419,709 (Mao et al., "Biodegradable Terephthalate Polyester-Poly(Phosphite) Compositions, Articles, and Methods of Using the Same). Biodegradable terephthalate polyester can also be used that include a phosphoester linkage that is a phosphonate. Suitable terephthalate polyester-poly(phosphonate) copolymers are described, for example, in U.S. Pat. Nos. 6,485,737 and 6,153,212 (Mao et al., "Biodegradable Terephthalate Polyester-Poly(Phosphonate) Compositions, Articles and Methods of Using the Same). Biodegradable terephthalate polyesters can be used that include a phosphoester linkage that is a phosphate. Suitable terephthalate polyester-poly(phosphate) copolymers are described, for example, in U.S. Pat. Nos. 6,322,797 and 6,600,010 (Mao et al., "Biodegradable Terephthalate Polyester-Poly(Phosphate) Polymers, Compositions, Articles, and Methods for Making and Using the Same).

Biodegradable polyhydric alcohol esters can also be used (See U.S. Pat. No. 6,592,895). This patent describes biodegradable star-shaped polymers that are made by esterifying polyhydric alcohols to provide acyl moieties originating from aliphatic homopolymer or copolymer polyesters. The biodegradable polymer can be a three-dimensional crosslinked polymer network containing hydrophobic and hydrophilic components which forms a hydrogel with a crosslinked polymer structure, such as that described in U.S. Pat. No. 6,583,219. The hydrophobic component is a hydrophobic macromer with unsaturated group terminated ends, and the hydrophilic polymer is a polysaccharide containing hydroxy groups that are reacted with unsaturated group introducing compounds. The components are convertible into a one-phase crosslinked polymer network structure by free radical polymerization. In yet further embodiments, the biodegradable polymer can comprise a polymer based upon $\alpha$-amino acids (such as elastomeric copolyester amides or copolyester urethanes, as described in U.S. Pat. No. 6,503,538).

In some aspects, the polymeric material is a hydrophobic polymer that can provide certain properties to the biocompatible layer, including pliability and drug-releasing properties. In some aspects of the invention, the hydrophobic polymer is present in the biocompatible layer in an amount sufficient to provide good pliability to the coating. Any suitable hydrophobic polymers can be used, and in many cases, can be chosen from those described herein.

In some preferred aspects, the amount of hydrophobic polymer is present in the biocompatible coated layer in the range of about 40% to about 90% (as based on total weight of the coated layer, and more preferably in the range of about 75% to about 90%.

In some embodiments, the bioactive agent-releasing layer can include one or more bioactive agents. In preferred aspects, the bioactive agent is released by particle dissolution or diffusion. It is understood that the release of the bioactive agent will generally include the bioactive agent passing through the biocompatible layer before being release locally into the adjacent or surrounding tissue.

In some embodiments, the coating includes a bioactive agent-releasing layer which includes a bioactive agent that can be prepared in combination with the polymeric materials of the bioactive agent coating composition. Preferably the bioactive agent can be released from the coating, including the biocompatible portion of the coating, in a controlled manner. Exemplary and preferred bioactive agents include, but are not limited to, antibiotics, anti-inflammatory agents, anti-proliferative agents, immunomodulatory agents, and anti-mitotics. Particularly useful bioactive agents of these classes include macrolide antibiotics such as rapamycin (triene macrolide antibiotic) and rapamycin analogs; immunomodulatory agents such as ABT-578; and anti-mitotics including taxoid drugs such as paclitaxel and docetaxel. Other useful bioactive agents are discussed herein.

In other embodiments, the coating composition can include one or more bioactive agents, or one or more bioactive agents can be added to the coating composition. The bioactive agent can be released by particle dissolution or diffusion when bio-stable matrices are used, or during polymer breakdown when absorbed into a biodegradable substance. Alternatively, one or more bioactive agents can be presented to the physiological environment without being released from the polymeric material. For example, the bioactive agent(s) can be covalently coupled to the polymeric material so that the agent(s) are not released from the polymeric material into the physiological environment.

The coating composition on the medical device can comprise one or more bioactive agents incorporated into a polymeric material so that the bioactive agent is presented to or released locally into the adjacent or surrounding tissue. If released, the bioactive agent is preferably released in a slow or controlled-release manner, to provide the desired elution profile to achieve the therapeutic effect. The release of the bioactive agent in a controlled release manner allows for smaller amounts of the bioactive agent to be released for a long period of time in a zero order elution profile manner. The release kinetics of the bioactive agent can further depend upon such factors as the hydrophobicity of the bioactive agent (for example, a more hydrophobic bioactive agent typically exhibits a slower the rate of release from the polymeric material). Alternatively, hydrophilic bioactive agents can be released from the polymeric material at a faster rate. Therefore, the polymeric composition can be altered according to the bioactive agent to be delivered in order to maintain the desired concentration of bioactive agent required at the treatment site for a longer period of time. As will be apparent upon review of this disclosure, the medical device can therefore provide a long-term effect of the bioactive agent at the treatment site that is more efficient in preventing restenosis and reduces side effects of the bioactive agents utilized.

An improvement in the function of a bioactive agent-releasing coating may be seen when the biocompatible layer minimizes the accumulation of blood components that may otherwise get deposited on the bioactive agent releasing layer. By reducing these factors, this may improve the function of the bioactive agent releasing layer.

For purposes of the description herein, reference will be made to "bioactive agent," but it is understood that the use of the singular term does not limit the application of bioactive agents contemplated, and any number of bioactive agents can be provided using the teaching herein. As used herein, "bioactive agent" refers to an agent that affects physiology of biological tissue. Bioactive agents useful according to the invention include virtually any substance that possesses desirable therapeutic characteristics for application to the implantation site.

It is important to note that the local delivery of combinations of bioactive agents may be utilized to treat a wide variety of conditions utilizing any number of medical devices, or to enhance the function and/or life of the device. Essentially, any type of medical device may be coated in some fashion with one or more bioactive agents that enhances treatment over use of the singular use of the device or bioactive agent.

The word "bioactive agent," as used herein, will refer to a wide range of biologically active materials or drugs that can be incorporated into a coating composition of the present invention. The bioactive agent(s) to be incorporated preferably do not chemically interact with the coating composition during fabrication or during the bioactive agent release process.

The term "bioactive agent," in turn, will refer to a synthetic inorganic or organic molecule that causes a biological effect when administered in vivo to an animal, including but not limited to birds and mammals, including humans. Nonlimiting examples are antigens, enzymes, hormones, receptors, peptides, and gene therapy agents. Examples of suitable gene therapy agents include a) therapeutic nucleic acids, including antisense DNA and antisense RNA, and b) nucleic acids encoding therapeutic gene products, including plasmid DNA and viral fragments, along with associated promoters and excipients. Examples of other molecules that can be incorporated include nucleosides, nucleotides, antisense, vitamins, minerals, and steroids.

Coating compositions prepared according to this process can be used to deliver drugs such as nonsteroidal anti-inflammatory compounds, anesthetics, chemotherapeutic agents, immunotoxins, immunosuppressive agents, steroids, antibiotics, antivirals, antifungals, steroidal antiinflammatories, and anticoagulants. For example, hydrophobic drugs such as lidocaine or tetracaine can be included in the coating and are released over several hours.

Classes of medicaments which can be incorporated into coatings of this invention include, but are not limited to, anti-AIDS substances, anti-cancer substances, antibiotics, anti-viral substances, enzyme inhibitors, neurotoxins, opioids, hypnotics, antihistamines, immunosuppressants (e.g., cyclosporine), tranquilizers, anti-convulsants, muscle relaxants and anti-Parkinson substances, anti-spasmodics and muscle contractants, miotics and anti-cholinergics, immunosuppressants (e.g. cyclosporine), anti-glaucoma solutes, anti-parasite and/or anti-protozoal solutes, anti-hypertensives, analgesics, anti-pyretics and anti-inflammatory agents (such as NSAIDs), local anesthetics, ophthalmics, prostaglandins, anti-depressants, anti-psychotic substances, anti-emetics, imaging agents, specific targeting agents, neurotransmitters, proteins, and cell response modifiers. A more complete listing of classes of medicaments may be found in the Pharmazeutische Wirkstoffe, ed. A. Von Kleemann and J. Engel, Georg Thieme Verlag, Stuttgart/New York, 1987, incorporated herein by reference.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, cephalosporins, geldanamycin, and analogs thereof. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Anti-viral agents are substances capable of destroying or suppressing the replication of viruses. Examples of anti-viral agents include α-methyl-P-adamantane methylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine.HCl, tacrine, 1-hydroxymaleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl, L(−), deprenyl HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacin, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−), alpha-methyltyrosine, D L(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances which have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label which is detectable in vivo, e.g., antibodies attached to fluorescent labels. The term antibody includes whole antibodies or fragments thereof.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Additives such as inorganic salts, BSA (bovine serum albumin), and inert organic compounds can be used to alter the profile of bioactive agent release, as known to those skilled in the art.

The bioactive (e.g., pharmaceutical) agents useful in the present invention include virtually any therapeutic substance that possesses desirable therapeutic characteristics for application to the implant site. These agents include: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives (including antiangiogenesis agents), anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, gene therapy agents, and statins (such as lovastatin, pravastatin, simvastatin, fluvastatin, atorvastatin, cerivastatin, rousvastatin, and superstatin) Other examples of suitable bioactive agents include sirolimus (rapamycin), analogues of rapamycin ("rapalogs"), tacrolimus, ABT-578 from Abbott, everolimus, paclitaxel, taxane, dexamethasone, betamethasone, paclitaxel, vinblastine, vincristine, vinorelbine, poside, teniposide, dactinomycin (actinomycin D), daunorubicin, doxorubicin, idarubicin, anthracyclines, mitoxantrone, bleomycins, plicanycin (mithramycin), mitomycin, mechlorethamine, cyclophosphamide and its analogs, melphalan, chlorambucil, ethylenimines and methylmelamines, alkyl sulfonates-busulfan, nirtosoureas, carmustine (BCNU) and analogs, streptozocin, trazenes-dacarbazinine, methotrexate, fluorouracil, floxuridine, cytarabine, mercaptopurine, thioguanine, pentostatin, 2-chlorodeoxyadenosine, cisplatin, carboplatin, procarbazine, hydroxyurea, mitotane, aminoglutethimide, estrogen, heparin, synthetic heparin salts, tissue plasminogen activator, streptokinase, urokinase, aspirin, dipyridamole, ticlopidine, clopidogrel, abciximab, breveldin, cortisol, cortisone, fludrocortisone, prednisone, prednisolone, 6U-methylprednisolone, triamcinolone, aspirin, acetaminophen, indomethacin, sulindac, etodalac, tolmetin, diclofenac, ketorolac, ibuprofen and derivatives, mefenamic acid, meclofenamic acid, piroxicam, tenoxicam, phenylbutazone, oxyphenthatrazone, nabumetone, auranofin, aurothioglucose, gold sodium thiomalate, cyclosporine, tacrolimus (FK-506), azathioprine, mycophenolate mofetil, vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

A comprehensive listing of bioactive agents can be found in *The Merck Index*. Thirteenth Edition, Merck & Co. (2001). Bioactive agents are commercially available from Sigma Aldrich Fine Chemicals, Milwaukee, Wis.

The concentration of the bioactive agent or agents dissolved or suspended in the coating mixture can range from about 0.01 to about 90 percent, by weight, based on the weight of the final coated composition.

The particular bioactive agent, or combination of bioactive agents, can be selected depending upon one or more of the following factors: the application of the controlled delivery device, the medical condition to be treated, the anticipated duration of treatment, characteristics of the implantation site, the number and type of bioactive agents to be utilized, and the like.

In some aspects, the coating includes a bioactive agent-releasing layer which can be adjacent to one or more other coated layers which can optionally be present in the coating. (For purposes of discussion, and also to describe various aspects of the invention, the coated layers may also be described by "first coated layer", "second coated layer", and, if necessary, so forth. However, the nomenclature that is used may be primarily for the convenience of describing various aspects of the invention. For example, when describing a coating with two layers, whether a "first layer" is distal or proximal to the surface of the device will be understood in the context of the specific description of that coating.)

If desired, optionally, the surface of the article can be treated to improve the association of components present in a subsequent coated layer. For example, the surface of the article may be pretreated with a silane-containing component (in these aspects, for example, this may be referred to as the first coated layer). In some cases, the coating can optionally include a base or "tie layer" that is between the surface of the article and the bioactive agent-releasing layer. The tie layer, which is optional, but present in some preferred embodiments, can improve the association of components that are subsequently coated on the article, such as components present in the bioactive-agent releasing layer. The tie layer can include a material, such as Parylene™ that is adhered or bonded to the surface of the article.

Optionally, in some embodiments of the invention, an intermediate coated layer can be present between the bioactive agent-releasing layer and the biocompatible layer. In some aspects, for example, when the bioactive agent-releasing layer is immediately adjacent to the (uncoated) surface of the article, this intermediate layer can be a "second coated layer", or one or more layers is present between the bioactive agent-releasing coating and the surface, this intermediate layer can be the third, fourth, etc., coated layer. This intermediate layer can include one or more compounds that are present in either, or both, of the bioactive agent-releasing layer and/or biocompatible layer. In some aspects, this coated layer can include a polymeric component present in the bioactive agent-releasing layer. For example, this intermediate layer can include poly(alkyl(meth)acrylates) having a short chain alkyl group, such as those in the range of $C_2$-$C_5$, including propyl ($C_3$), and most preferably butyl ($C_4$). Most preferably this intermediate layer includes preferably a poly(alkyl (meth)acrylate), such as pBMA.

Other coated layers may also be present between the bioactive agent-releasing layer and the biocompatible layer. Although these layers are optional, they may be formed to change or improve aspects of the coating.

In other embodiments of the invention, a bioactive agent can be added to, or is present in the coating composition. For example, in some aspects, a composition containing the polymeric material, a biocompatible agent, and a photoreactive moiety is prepared. The composition is then treated to couple the biocompatible agent to the polymeric material via the photoreactive group. After this treatment a bioactive agent is added to the composition. The composition containing the bioactive agent is then disposed on a substrate. Alternatively, the coating composition is first disposed on the substrate and then the bioactive agent is added to the coating.

The invention generally provides methods for preparing a biocompatible surface on a medical article. According to the invention, biocompatible agents can be selected to improve the compatibility (for example, with blood and surrounding tissues) of medical device surfaces. In preferred embodiments, the biocompatible agent, when coupled to the medical device surface, can serve to shield the blood from the underlying medical device material. Suitable biocompatible agents preferably reduce the likelihood for blood components to adhere to the medical device and activate, thus reducing the formation of thrombus or emboli (blood clots that release and travel downstream.

The biocompatible agent can be essentially any biomolecule that is attached to the solid surfaces of medical articles to improve biocompatibility of the medical article. Thus, the description of bioactive agents suitable for use in the polymeric material is instructive for selection of the biocompatible agents as well.

In some aspects, the biocompatible agent is a biocompatible polymer. According to the invention, biocompatible polymers can be selected to improve the compatibility (for example, with blood and surrounding tissues) of medical device surfaces. In preferred embodiments, the biocompatible polymer, when coupled to the medical device surface, can serve to shield the blood from the underlying medical device material. Suitable biocompatible polymers preferably reduce the likelihood for blood components to adhere to the medical device and activate, thus reducing the formation of thrombus or emboli (blood clots that release and travel downstream.

The biocompatible polymer can be essentially any polymer that can improve biocompatibility of the medical device.

Representative examples of biocompatible polymers (including peptides and proteins) having antithrombotic effects include heparin, heparin derivatives, sodium heparin, low molecular weight heparin, hirudin, polylysine, argatroban, glycoprotein IIb/IIIa platelet membrane receptor antibody, coprotein IIb/IIIa platelet membrane receptor antibody, recombinant hirudin, thrombin inhibitor (such as commercially available from Biogen), chondroitin sulfate, modified dextran, albumin, streptokinase, and tissue plasminogen activator (TPA).

Other contemplated biocompatible polymers include fibronectin, laminin, collagen, elastin, vitronectin, tenascin, fibrinogen, thrombospondin, osteopontin, von Willibrand Factor, bone sialoprotein and active domains thereof), or a hydrophilic polymer such as hyaluronic acid, chitosan or methyl cellulose.

Exemplary cell-cell adhesion molecules include N-cadherin and P-cadherin and active domains thereof.

Exemplary growth factors include fibroblastic growth factors, epidermal growth factor, platelet-derived growth factors, transforming growth factors, vascular endothelial growth factor, bone morphogenic proteins and other bone growth factors, and neural growth factors.

Exemplary ligands or receptors include antibodies, antigens, avidin, streptavidin, and biotin.

In some aspects, the biocompatible polymer is present in the coating in an amount sufficient to provide a therapeutically useful amount of biocompatible activity to the surface of the device. For example, in some aspects, the coating provides heparin activity in an amount that either prevents or reduces the accumulation of clotting factors over a period of time during which the device is used.

In some preferred aspects, the amount of hydrophilic biocompatible polymer (for example, heparin) is present in the biocompatible coated layer in the range of about 5% to about 25% (as based on total weight of the coated layer), and more preferably in the range of about 5% to about 15%.

In preferred aspects, the hydrophilic biocompatible polymer has one or more pendent photoreactive groups. The photoreactive group can be pendent from the polymer in an amount that allows for the formation of a stable coated layer that provides biocompatibility, such as heparin activity. One exemplary hydrophilic biocompatible polymer with pendent photoreactive groups is photo-heparin, which is-described herein. The hydrophilic biocompatible polymer with pendent photoreactive groups can be used with other photoreactive components in the biocompatible coating composition.

In some aspects, the method of providing a biocompatible coating to a medical device can also include a step of disposing a second biocompatible agent, which can be different or the same as the biocompatible agent of the coating compound, on the medical article, such as to provide a second coating to the medical article. The second biocompatible agent can include reactive groups such as photoreactive groups. The step of disposing a second biocompatible agent can provide a top coat to the medical article.

In a preferred aspect of the invention, a miscibility enhancer is added to the biocompatible coating composition. A miscibility enhancer can be used to improve the homogeneity of the polymeric material and the biocompatible agent in the coating composition and improve the overall coating composition. According to the invention, the miscibility enhancer can be used improve the coupling of the biocompatible agent to the polymer, for example, an adherent polymer.

The miscibility enhancer can be selected from the group consisting of polyvinylpyrrolidinone (PVP), polyethyleneglycol (PEG), PEG sulfonates, fatty quaternary amines, fatty sulfonates, fatty acids, dextran, dextrin, and cyclodextrin. The miscibility enhancer can also include pendant photoreactive groups.

Preferably, the miscibility enhancer is a polymeric material, in some aspects, is the third polymer of the biocompatible layer. A 1-vinyl-2-pyrrolidone homopolymer or copolymer is preferred, herein referred to as a "poly(vinylpyrrolidone)" (PVP). PVP is a tertiary amide based polymer. In some preferred aspects, the PVP component has a molecular weight of about $1 \times 10^6$ Da or less.

In some preferred aspects, the amount of PVP is present in the biocompatible coated layer in the range of about 5% to about 50% (as based on total weight of the coated layer), and more preferably in the range of about 5% to about 15%.

If a PVP copolymer is used, it can be a copolymer of VP and a monomer selected from the group of hydrophilic monomers. Exemplary hydrophilic monomers include (meth)acrylamide and (meth)acrylamide derivatives, such as alkyl (meth)acrylamide and aminoalkyl(meth)acrylamide, such as aminopropylmethacrylamide and dimethylaminopropylmethacrylamide. Use of PVP copolymers is particularly advantageous for the preparation and use of PVP derivitized with photoreactive groups.

PVP copolymers can be prepared to change the properties of PVP, for example, poly(vinylpyrrolidone-co-vinyl acetate) polymers can be prepared which can be more hydrophobic and gives less brittle films. Poly(vinylpyrrolidone) can be prepared by polymerization of 1-vinyl-2-pyrrolidone in water using hydrogen peroxide as an initiator. Methods for terminating the polymerization VP can allow the preparation of PVP of numerous molecular weights.

The coated layer also includes photoreactive groups that have been activated and reacted to bond to one or more compound(s) present in the coating. "Activated" means that the photoreactive groups have been treated with an activating sources of radiation, thereby having excited the groups to an active state which resulted in the bonding the groups to one or more other components in the coating composition. Use of photoreactive groups is particularly advantageous as used in the present invention for many reasons. For example, use of photoreactive groups allows the timing of bond formation to be controlled with high precision. For example, at one or more points during the coating process the photogroups can be activated for a desired length of time. Use of photoreactive groups also allows one to control the extent of bond formation by controlling the amount of applied activating energy. Knowing the composition of the coating and other materials associated with the coated surface, the use of photogroups can allow bond formation between particular targets and not others. Also, a photoreactive group can be chosen to absorb activating energy at particular wavelengths and not others. This can be beneficial if components, such as bioactive agents, in the coating are sensitive to particular wavelengths of light.

The photoreactive moiety can be pendent from the biocompatible agent or polymeric material. Alternatively, or additionally, the photoreactive moiety is independent of the polymeric material or the biocompatible agent in the coating composition.

In some embodiments the photoreactive moiety is independent of the polymeric material and the biocompatible material and can be, for example, a crosslinking agent. Exemplary crosslinking gents are described in Applicant's U.S. Pat. No. 5,414,075 (Swan et al.), and U.S. Publication No. 2003/0165613 Al (Chappa et al.). See also U.S. Pat. No. 5,714,360 (Swan et al.) and U.S. Pat. No. 5,637,460 (Swan et al.).

In one such embodiment described in these references, the crosslinking agent can comprise a chemical nonpolymeric core molecule having attached to it one or more first latent reactive groups and one or more second latent reactive groups.

In some preferred embodiments, the crosslinking reagent is selected from tetrakis (4-benzoylbenzyl ether), the tetrakis (4-benzoylbeonzoate ester) of pentaerythritol, and an acylated derivative of tetraphenylmethane.

A "latent reactive group," as used herein, refers to a chemical group that responds to an applied external energy source in order to undergo active specie generation, resulting in covalent bonding to an adjacent chemical structure (via an abstractable hydrogen). Preferred groups are sufficiently stable to be stored under conditions in which they retain such properties. See, for example, U.S. Pat. No. 5,002,582 (Guire et al.). Latent reactive groups can be chosen that are responsive to various portions of the electromagnetic spectrum, with those responsive to ultraviolet and visible portions of the spectrum (referred to herein as "photoreactive") being particularly preferred.

In preferred embodiments a photoreactive group is pendent from the biocompatible agent. In other preferred embodiments a photoreactive group is pendent from the miscibility enhancer or pendent from both the biocompatible agent and the miscibility enhancer.

Photoreactive species responds to a specific applied external ultraviolet or visible light source to undergo active specie generation with resultant covalent bonding to an adjacent chemical structure, for example, as provided by the same or a different molecule. Photoreactive species are those groups of atoms in a molecule that retain their covalent bonds unchanged under conditions of storage but that, upon activation by a specific applied external ultraviolet or visible light source form covalent bonds with other molecules.

Latent reactive (for example, photoreactive) species generate active species such as free radicals and particularly nitrenes, carbenes, and excited states of ketones, upon absorption of electromagnetic energy. Latent reactive species can be chosen to be responsive to various portions of the electromagnetic spectrum, and photoreactive species that are responsive to the ultraviolet and visible portions of the spectrum are preferred and can be referred to herein as "photoreactive groups" or "photoreactive moieties."

The latent reactive species in latent reactive aryl ketones are preferred, such as acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred latent reactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

In other embodiments, the photoreactive moiety is pendent from the polymeric material. For example, at least one photoreactive group is covalently bonded to the polymeric material. Polymeric material having pendent photoreactive groups can be coupled to a component, such as the biocompatible agent, or more than one moiety, by activating one or more of the photoreactive groups of the polymeric material.

Preparation of polymeric material, biocompatible agents, or miscibility enhancers having pendent photoreactive groups can be achieved by a variety of different methods. For example, a polymer (such as a polymeric miscibility enhancer) having pendent photoreactive groups can be first prepared by preparing a copolymer and then reacting the copolymer with compounds that lead to the photoderivitization of the copolymer.

For example, an photoreactive polymer can be formed by reacting acrylamide, 2-acrylamide-2-methylpropane sulfonic acid, and N-3-aminopropyl)methacrylamide to form a copolymer. The copolymer is derivatized with an acyl chloride (such as, for example, 4-benzoylbenzoyl chloride) under Schotten-Baumann conditions. That is, the acyl chloride reacts with the amino group of the N-(3-aminopropyl) moiety of the copolymer. An amide is formed resulting in the attachment of the aryl ketone to the polymer.

Photo-poly(vinylpyrrolidone) (also referred to as "photo-PVP") can be formed by the copolymerization of 1-vinyl-2-pyrrolidone and N-(3-aminopropyl(meth)acrylamide), which then can be derivatized with an acyl chloride (such as, for example, 4-benzoylbenzoyl chloride) under Schotten-Baumann conditions. That is, the acyl chloride reacts with the amino group of the N-(3-aminopropyl) moiety of the copolymer. An amide is formed resulting in the attachment of the aryl ketone to the polymer. Photo-PVP is commercially available, from SurModics, Inc., Eden Prairie, Minn., or can be synthesized.

Photoderivatized polysaccharides, such as heparin ("photoheparin") can be prepared by those skilled in the art as well, for example, in the manner described in U.S. Pat. No. 5,563,056 (Swan et al., see Example 4), which describes the preparation of photoheparin by reacting heparin with benzoyl-benzoyl-epsilon-aminocaproyl-N-oxysuccinimde in dimethylsulfoxide/carbonate buffer. The solvent was evaporated and the photoheparin was dialyzed against water, lyophilized, and then dissolved in water.

Other photoderivatized biocompatible agents, such as collagen, fibronectin, and laminin can be prepared as described. See, for example, U.S. Pat. No. 5,744,515 (Clapper, Method and Implantable Article for Promoting Endothelialization). As described in this patent, a heterobifunctional crosslinking agent can be used to photoderivatize a protein, such as a biocompatible agent. The crosslinking agent includes a benzophenone photoactivatable group on one end (benzoyl benzoic acid, BBA), a spacer in the middle (epsilon aminocaproic acid, EAC), and an amine reactive thermochemical coupling group on the other end (N-oxysuccinimide, NOS). BBA-EAC is synthesized from 4-benzoylbenzoyl chloride and 6-aminocaproic acid. Then the NOS ester of BBA-EAC is synthesized by esterifying the carboxy group of BBA-EAC by carbodiimide activation with N-hydroxysuccimide to yield BBA-EAC-NOS. Proteins, such as collagen, fibronectin, laminin, and the like can be obtained from commercial sources. The protein is photoderivatized by adding the BBA-EAC-NOS crosslinking agent at a ratio of 10-15 moles of BBA-EAC-NOS per mole of protein.

Typically, the reacted photogroups present in the biocompatible layer couple one or more components present in the coating together. For example, in some embodiments, the reacted photogroups can couple the biocompatible polymer to the hydrophobic polymer and/or PVP, and/or can couple the PVP polymer to the biocompatible polymer and/or the hydrophobic polymer. The biocompatible coating can be formed with the reactive photogroups being pendent from one or more of the polymeric components (and bonded to another coated component), the reacted photogroups being independent of any component in the coating composition, or both. In a preferred aspect the coating composition is formed using reactive photogroups that are pendent from the biocompatible polymer, the PVP polymer, and most preferably both the biocompatible polymer and the PVP polymer.

In yet other embodiments the photoreactive moiety is independent of the biocompatible polymer and the polymeric material. For example, the photoreactive moiety can be a molecule having at least one photoreactive group that is able to couple the biocompatible polymer to the polymeric material when activated. One example is a crosslinking agent that includes two or more photoreactive groups.

Preferred activated photogroups are selected from activated aryl ketones, for example, activated benzophenone.

In order to provide a preferred coating, a coating composition can be prepared to include a solvent or dispersant, polymeric material that can include one or more polymers, the biocompatible agent, the bioactive agent(s), and the photoreactive moiety. Solvents or dispersant that can be included in the coating composition include, but are not limited to, alcohols (e.g., methanol, ethanol, n-propanol and isopropanol), alkanes (e.g., halogenated or unhalogenated alkanes such as hexane, heptane, cyclohexane, methylene chloride and chloroform), amides (e.g., dimethylformamide, N-methylpyrrolidone), ethers (e.g., tetrahydrofuran (THF), dipropyl ether and dioxolane), ketones (e.g., methyl ethyl ketone, methyl isobutyl ketone), aromatic compounds (e.g., toluene and xylene), nitriles (e.g., acetonitrile), and ester (e.g., ethyl acetate and butyl acetate).

In another aspect of the invention, it has been found that isopropanol is particularly useful as a component in the coating composition. It has been found that solutions or suspensions of the adherent polymer and the biocompatible agent, and also the miscibility enhancer, can be prepared that include isopropanol and then mixed together in order to prepare the coating composition. For example, isopropanol can be present in an amount of 50% or greater, 60% or greater, 70% or greater, 80% or greater, or most preferably 85% or greater of the amount of solvent or dispersant present in the composition (volume/volume). Isopropanol can be present in combination with other solvents or dispersants, for example water or THF. In some embodiments, the solvents include a mixture of isopropanol, water, and THF. In some embodiments isopropanol is present in an amount of 85% or greater, water is present in an amount of 1% or greater, and THF is present in an amount of 1% or greater of the total solvents.

Therefore, in yet another aspect, the invention provides a coating composition comprising (a) heparin, (b) a polymeric material comprising monomeric units selected from alkyl acrylates and alkyl methacrylates, and (c) photoreactive moiety, wherein the photoreactive moiety is either coupled to (a), (b), both (a) and (b), or is independent; and isopropanol. In some embodiments, the coating composition can also include tetrahydrofuran.

In one preferred method for preparing the coating composition, solutions of the polymeric components are individually prepared and then combined. In a first solution, the hydrophobic polymer, preferably a poly(alkyl(meth)acrylate) such as poly(butyl(meth)acrylate), is dissolved or suspended in a solvent selected from the group consisting of tetrahydrofuran (THF) and acetone. Most preferably the hydrophobic polymer is dissolved in THF. In a second solution, a hydrophilic biocompatible polymer, preferably a biocompatible polysaccharide such as heparin, is dissolved or suspended in a protic solvent, preferably water. In third solution poly(vinylpyrrolidone) is dissolved or suspended in a solvent selected from the group consisting of water, diethylene glycol, methanol, ethanol, n-propanol, isopropanol (IPA), n-butanol, chloroform, methylene chloride, 2-pyrrolidone, polyethylene glycol, propylene glycol, 1,4-butanediol, glycerol, triethanolamine, propionic acid, and acetic acid; in a preferred aspect the solvent is IPA.

Next, the second solution (hydrophilic biocompatible polymer) solution and the third solution (PVP) are combined to form a mixture; this mixture is then added to the first solution (hydrophobic polymer).

In some aspects, the invention provides a coating composition including polymeric components comprising (i) a hydrophobic polymer, preferably a poly(alkyl(meth)acrylate such as pBMA; (ii) a hydrophilic biocompatible polymer, preferably heparin; (iii) a PVP polymer; and (iv) photoreactive groups, wherein the photoreactive groups are preferably pendent from (ii) or (iii), or both (ii) and (iii), and wherein the polymeric components are present solvent system comprising (a) a first liquid selected from tetrahydrofuran (THF) and acetone; and (b) a second liquid selected from water, diethylene glycol, methanol, ethanol, n-propanol, isopropanol (IPA), n-butanol, chloroform, methylene chloride, 2-pyrrolidone, polyethylene glycol, propylene glycol, 1,4-butanediol, glycerol, triethanolamine, propionic acid, and acetic acid. Preferably the second liquid is selected from $C_1$-$C_4$ alcohols such as methanol, ethanol, n-propanol, isopropanol (IPA), and n-butanol. Most preferably the second liquid is IPA.

In a more preferred embodiment the polymeric components, as described, are present in a solvent system comprising (a) a first liquid selected from tetrahydrofuran (THF) and acetone; and (b) a second liquid selected from water, diethylene glycol, methanol, ethanol, n-propanol, isopropanol (IPA), n-butanol, chloroform, methylene chloride, 2-pyrrolidone, polyethylene glycol, propylene glycol, 1,4-butanediol, glycerol, triethanolamine, propionic acid, and acetic acid, and (c) water.

In another preferred embodiment, the polymeric components are present in a solvent system comprising (a) a first liquid selected from tetrahydrofuran (THF) and acetone; and (b) $C_1$-$C_4$ alcohols such as methanol, ethanol, n-propanol, isopropanol (IPA), and n-butanol, and (c) water.

In another preferred embodiment, the polymeric components are present in a solvent system comprising (a) tetrahydrofuran; and (b) isopropanol (IPA), and (c) water.

The first liquid (i.e., THF or acetone) is preferably present in the solvent system at a concentration of 50% or greater, preferably in the range of 50% to 90%, and even more preferably in the range of about 60% to about 80%. Preferably the first liquid is THF.

The second liquid, if, for example, present in a binary solvent system with the THF or acetone, is present at a concentration of 50% or less, preferably in the range of 50% to 10%, and even more preferably in the range of about 40% to about 20%.

A most preferred solvent system includes a (i) first liquid selected from THF or acetone present in the solvent system at a concentration of 50% or greater, preferably in the range of 50% to 90%, and even more preferably in the range of about 60% to about 80%; a second liquid selected from diethylene glycol, methanol, ethanol, n-propanol, isopropanol (IPA), n-butanol, chloroform, methylene chloride, 2-pyrrolidone, polyethylene glycol, propylene glycol, 1,4-butanediol, glycerol, triethanolamine, propionic acid, and acetic acid, present in the solvent system at a concentration of 35% or less, preferably in the range of 5% to 30%; and water at a concentration of 20% or less, for example, in the range of 0.1 % to 20%, more preferably in the range of 0.1 % to 2%. One example of a suitable ternary solvent system consists of 60% THF, 25% EPA, and 15% water.

The polymeric components can be combined in any manner that would allow formation of a coating composition suitable for forming a biocompatible layer. However, it has been discovered that some methods of preparing the biocompatible coating composition provide a biocompatible coating composition that can be deposited on the surface of an article and provide excellent biocompatible features.

In more specific aspects, the invention provides compositions having polymeric components present in amounts in defined ranges. Particularly useful ranges for the hydrophobic polymer, for example, the poly(alkyl(meth)acrylate) polymer, are at concentrations in the range of 1-20 mg/mL, more preferably in the range of 2.5-10 mg/mL, and most preferably in the range of 2.5-7.5 mg/mL The hydrophilic biocompatible polymer (e.g., heparin) is preferably present in an amount of 0.1 mg/mL or greater, for example in the range of 0.1-10.0 mg/mL, and preferably in the range of 0.25 to 1.5 mg/mL. Particularly useful ranges for PVP is in the range of 0.1-2.5 mg/mL, and preferably in the range of 0.1-1.0 mg/mL.

According to the invention, at least a portion of the surface of the medical article is coated with the coating composition. In some embodiments, the entire surface of the medical article can be coated with the coating composition. The amount of the surface area provided with the polymeric material can be determined according to such factors as the medical device to be utilized, the application of the device, the bioactive agent to be utilized with the polymeric material, and the like factors.

Coating compositions described herein that include polymeric materials having any combination polymers, biocompatible agents, and desired bioactive agents can be provided to the surface of the medical article, depending upon the final application of the medical device. The coating composition (with or without bioactive agent) can be applied to the medical device using standard techniques to cover the entire surface of the device, or a portion of the device surface. Further, the coating composition can be disposed on the medical article as a single layer (with or without bioactive agent) or in combination with other layers (with or without bioactive agent). When multiple layers are provided on the surface, each individual layer can include one or more components chosen to provide a desired effect. In some embodiments, each layer is composed of the same polymeric materials. Alternatively, one or more of the layers is composed of a polymeric material that is different from one or more of the other layers. Additionally, multiple layers of various bioactive agents can be deposited onto the medical device surface so that a particular bioactive agent can be presented to or released from the medical device at one time. Application techniques for the coating of polymeric material include, for example, dipping, spraying, and the like. The suitability of the coating composition for use with a particular medical article, and in turn, the suitability of the application technique, can be evaluated by those skilled in the art, given the present description.

In some aspects of the invention, the biocompatible layer comprises at least three polymers. Of the three, the first polymer is a hydrophobic polymer which can be selected from the group of poly(meth)acrylates. In a preferred aspect the first polymer is a poly(alkyl(meth)acrylate) having a short chain, such as those in the range of $C_2$-$C_5$, including propyl ($C_3$), and most preferably butyl ($C_4$). Most preferably the first polymer is poly(butyl(meth)acryate) (pBMA). In some cases, and preferably, the first polymer of the biocompatible layer can be the same as the hydrophobic polymer of the bioactive agent-releasing layer. For example the hydrophilic polymer of the bioactive agent-releasing layer and the biocompatible layer is pBMA.

Therefore, in some aspects, the invention provides a method of providing a biocompatible bioactive agent releasing coating, the method including the steps of (a) disposing bioactive agent composition comprising a bioactive agent and a hydrophobic polymer, preferably a poly(alkyl(meth)acrylate), on an article to form a bioactive agent-releasing layer and (b) disposing a biocompatible coating composition comprising (i) a hydrophobic polymer, (ii) a hydrophilic biocompatible polymer, and (iii) PVP, wherein the photoreactive moiety is pendent from (ii) or (iii). In some cases the method of forming the coating can include one or more other steps of forming a coated layer that is different than the bioactive agent-releasing layer or the biocompatible layer. These optional steps can include, for example, a step of forming a tie layer or a step of forming an intermediate layer.

In some cases the composition is pre-irradiated, that is, the composition is irradiated prior to being disposed on the surface of an article.

For example, a composition including photo-heparin and photo-PVP is irradiated to activate the photoreactive groups; subsequently the composition is disposed on the surface of the device. Therefore, in this preferred aspect, a preferred method of coating comprises the steps of (a) providing a coating composition comprising (i) a hydrophobic polymer, (ii) a hydrophilic biocompatible polymer, and (iii) PVP, wherein the photoreactive moiety is pendent from (ii) or (iii); (b) after step (a) treating the coating composition to activate the photoreactive moiety, and (c) after step (b) disposing the coating composition on the surface of the medical article. One or more other steps can be include in this method which can be performed before, after, or in between steps (a)-(c).

In some cases, irradiation may occur before or after disposing the coating composition.

In other aspects, the invention provides methods of providing a biocompatible coating to a surface of a medical article. The methods comprise the steps of (a) providing a coating composition comprising (i) a hydrophobic polymer, (ii) a hydrophilic biocompatible polymer, and (iii) PVP, wherein the photoreactive moiety is pendent from (ii) or (iii); (b) disposing the coating composition on the surface of the medical article; and (c) treating the coating composition to activate the photoreactive moiety. In a preferred aspect, the coating composition comprises a solvent system comprising (i) a first liquid selected from THF or acetone, (ii) IPA, and (iii) water.

In another aspect, the invention provides a coating composition that can be used to form a layer that provides biocompatibility to all or a portion of a surface of an article. The coating composition includes at least the components that are used to form a biocompatible layer on the surface of an article.

In some aspects of the invention, the coating composition includes a bioactive agent and the step of treating the composition is performed after the coating composition is deposited on the surface of the medical article. In these aspects a method comprising steps of determining information indicative of wavelength of light that causes inactivation of the bioactive agent, and using the wavelength information obtained to select a filter for coupling photoreactive agents to the polymeric material containing the bioactive agent. According to these embodiments, inactivation of the bioactive agent means degradation of the bioactive agent sufficient to reduce or eliminate the therapeutic effectiveness of the bioactive agent.

In some aspects of the invention, the methods and compositions can be particularly useful for providing coatings to surfaces of medical devices, the coating providing features and that incorporates a polymeric material that can be deposited and adhered to a surface. While adhering to the substrate surface, the polymer of the coating composition also allows the biocompatible agent to be stably presented on the surface of the coated article. Since a treatment step is not necessary after the coating composition is deposited on the surface of the substrate, this may allow a bioactive agent to be incorporated into the coating composition without subjecting the bioactive agents to a treatment step, thereby reducing the possibility of degradation of the bioactive agents by the treatment.

In addition, the polymeric material of the coating composition can be useful for controllably releasing one or more bioactive agents from the biocompatible coating. A coating composition containing polymeric material having both adherent and drug-releasing properties and a biocompatible agent can be prepared. After the composition is prepared a bioactive agent can be incorporated into the composition. The coating composition can be deposited on a substrate to provide a biocompatible and drug-releasing coating.

A coating with these properties can surprisingly be formed on a surface of a medical device in a minimal number of steps. This greatly reduces the throughput time for the fabrication of medical articles having these features and can result in a substantial cost savings as many reagents and steps that might typically be attempted in fabrication of these coated medical articles are not necessarily required.

The compositions and methods of the invention provided coatings that were readily prepared and that demonstrated excellent biocompatible and wettability characteristics. For example, stents coated with compositions according to the invention demonstrated substantial heparin or collagen surface activities.

In preferred embodiments, the coating composition includes a bioactive agent or the method of coating further comprises a step of adding a bioactive agent to the coating composition. In some aspects the bioactive agent is added to the coating composition after the step of treating the coating composition has been performed. The bioactive agent can be released from or presented by the coating once the coating is formed on the medical article and implanted in a patient. In some embodiments, the coating composition can include more than one bioactive agent, wherein each of the bioactive agents can be independently selected depending upon the desired therapeutic application of the invention.

In the step of treating, the photoreactive moieties can be activated by irradiation using a suitable light source. In some aspects of the invention, photoreactive group can be activated using a filtered light source. A useful filtered light source provides wavelengths of light that are greater than the wavelength at which the bioactive agent maximally absorbs light.

In some embodiments, the coating composition includes a bioactive agent or the method further comprises a step of adding a bioactive agent to the coating composition. In some aspects the bioactive agent is added to the coating composition after the step of treating the coating composition has been performed. The invention contemplates various embodiments for forming a biocompatible coating, also including a bioactive agent, some of which are now described in greater detail.

In another particular aspect of the invention, the method includes the steps of (a) providing a coating composition comprising a polymer selected from the groups consisting of includes poly(alkyl(meth)acrylates) and poly(aromatic (meth)acrylates) and a biocompatible agent comprising at least one photoreactive moiety; (b) treating the coating composition to activate the photoreactive group; (c) adding a bioactive agent to the coating composition; and (d) disposing the coating composition on the surface of the medical article.

In another particular aspect of the invention, the method includes the steps of (a) providing a coating composition comprising an adherent polymer and a biocompatible agent comprising at least one photoreactive moiety; (b) treating the coating composition to activate the photoreactive group; (c) adding a bioactive agent to the coating composition; and (d) disposing the coating composition on the surface of the medical article.

In another particular aspect of the invention, the method includes the steps of (a) providing a coating composition comprising an adherent polymer and a polysaccharide comprising at least one photoreactive moiety; (b) treating the coating composition to activate the photoreactive group; (c) adding a bioactive agent to the coating composition; and (d) disposing the coating composition on the surface of the medical article.

In another particular aspect of the invention, the method includes the steps of (a) providing a coating composition comprising an adherent polymer and a protein or peptide comprising at least one photoreactive moiety; (b) treating the coating composition to activate the photoreactive group; (c)

adding a bioactive agent to the coating composition; and (d) disposing the coating composition on the surface of the medical article.

In another particular aspect of the invention, the method includes the steps of (a) providing a coating composition comprising a polymer having alkyl acrylate or alkyl methacrylate monomeric units and a biocompatible agent comprising at least one photoreactive moiety; (b) treating the coating composition to activate the photoreactive group; (c) adding a bioactive agent to the coating composition; and (d) disposing the coating composition on the surface of the medical article.

In another particular aspect of the invention, the method includes the steps of (a) providing a coating composition comprising a polymer having alkyl acrylate or alkyl methacrylate monomeric units, and heparin comprising at least one photoreactive moiety; (b) treating the coating composition to activate the photoreactive group; (c) adding a bioactive agent to the coating composition; and (d) disposing the coating composition on the surface of the medical article.

In another particular aspect of the invention, the method includes the steps of (a) providing a coating composition comprising a polymer having alkyl acrylate or alkyl methacrylate monomeric units, and collagen comprising at least one photoreactive moiety; (b) treating the coating composition to activate the photoreactive group; (c) adding a bioactive agent to the coating composition; and (d) disposing the coating composition on the surface of the medical article.

The invention contemplates various embodiments for forming a biocompatible coating, wherein the presence of a bioactive agent is optional, but not required. Alternatively, in some aspects a bioactive agent can be disposed before or after disposing the biocompatible coating composition.

In another embodiment, the method includes the steps of (a) providing a coating composition comprising (i) an adherent polymer, (ii) miscibility agent selected from the group consisting of polyvinylpyrrolidinone (PVP), polyethyleneglycol (PEG), PEG sulfonates, fatty quaternary amines, fatty sulfonates, fatty acids, dextran, dextrin, and cyclodextrin, (iii) a biocompatible agent, and (iv) a photoreactive moiety, and wherein the photoreactive moiety is pendent from (i), pendent from (ii), pendent from (iii), independent, or combinations thereof; (b) disposing the coating composition on the surface of the medical article; and (c) treating the coating composition to activate the photoreactive group.

In another particular embodiment, the method includes the steps of (a) providing a coating composition comprising (i) an adherent polymer, (ii) polyvinylpyrrolidone, (iii) a biocompatible agent, and (iv) a photoreactive moiety, and wherein the photoreactive moiety is pendent from (i), pendent from (ii), pendent from (iii), independent, or combinations thereof; (b) disposing the coating composition on the surface of the medical article; and (c) treating the coating composition to activate the photoreactive group.

In some aspects, an outer coating ("topcoat") of biocompatible agent can be applied to the coated composition. The outer coating can be provided on a portion of, or the entirety of, the medical article surface.

In the step of treating, the photoreactive moieties can be activated by irradiation using a suitable light source. In some aspects of the invention, photoreactive group can be activated using a filtered light source. A useful filtered light source provides wavelengths of light that are greater than the wavelength at which the bioactive agent maximally absorbs light.

In some embodiments, a filter is utilized in connection with the step of treating, which can involve the activation of the one or more photoreactive groups. In embodiments wherein a bioactive agent is included in the coating composition, the one or more photoreactive groups are activated by providing light having a wavelength selected in a range to activate the photoreactive groups and minimize inactivation of bioactive agent in the polymeric material.

In one such embodiment, for example, a medical article having a polymeric material disposed on at least a portion of its surface is provided, wherein the polymeric material includes a bioactive agent. In one illustrative example, the bioactive agent is an analog of rapamycin (also referred to herein as a "rapalog"). It can be determined that rapamycin is inactivated at wavelengths in the range of 300 nm or less. This information can be utilized in combination with information relating to electromagnetic energy sufficient to activate photoreactive agents (for example, to undergo active specie generation with resultant covalent bonding to an adjacent chemical structure) as described herein (for example, having activation wavelengths in the UV and visible portions of the spectrum, such as in the range of 100-700 nm, or 300-600 nm, or 200-400 nm, or 300-340 nm). The combined information can then be utilized to select an appropriate light filter for application of photoreactive species to the polymeric material.

Information relating to the UV spectra at which a particular bioactive agent is degraded can be obtained, for example, by the provider of the bioactive agent, or by subjecting the bioactive agent to a variety of wavelengths of light, and determining the subsequent activity retained of the bioactive agent.

Typically, filters are identified by the wavelength of light that is permitted to pass through the filter. Two illustrative types of filters that can be used in connection with the invention are cut-off filters and band pass filters. Generally, cut-off filters are categorized by a cut-off transmittance, at which the light transmittance is approximately 25% of the maximum transmittance. For band pass filters, a range of wavelength is identified for the filter, and the center wavelength is the midpoint of wavelength allowed through; at midpoint, the transmittance is approximately half of the maximum transmittance allowed through the filter.

Thus, in one embodiment utilizing a band pass filter, for example, an Edmund 407 nm filter, the filter can be chosen that has a maximum UV transmittance at its center wavelength of 407 nm. From either direction from that, the UV transmittances decreases. Thus, towards 300 nm, the UV transmittance is not enough to cause significant degradation of the rapalog. This filter can be selected and utilized to couple a photoreactive reagent to a polymeric material containing rapamycin or a rapalog, as shown in the Examples. Other exemplary embodiments of this aspect of the invention can be found in the examples.

The invention will be further described with reference to the following non-limiting Examples.

EXAMPLES

For the following examples, the following standard reagents and nomenclature are adopted:

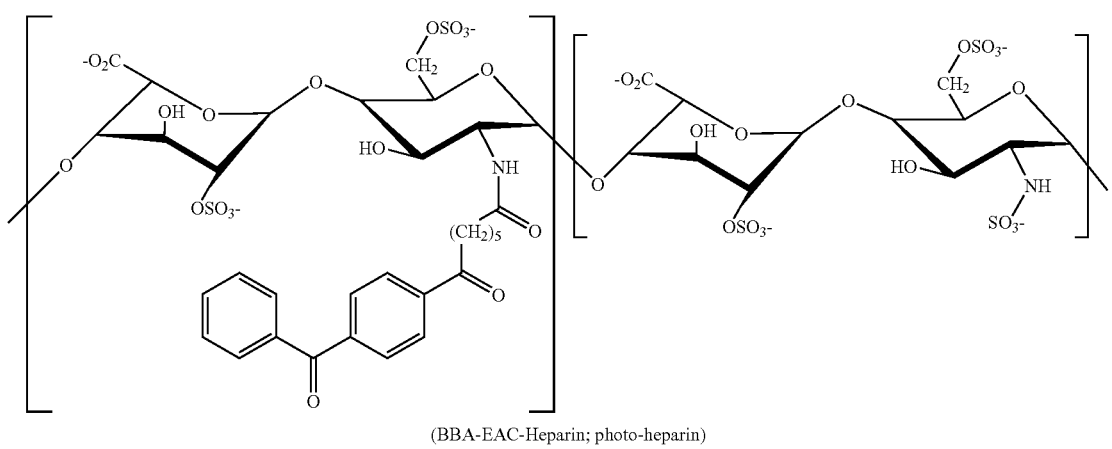
(BBA-EAC-Heparin; photo-heparin)
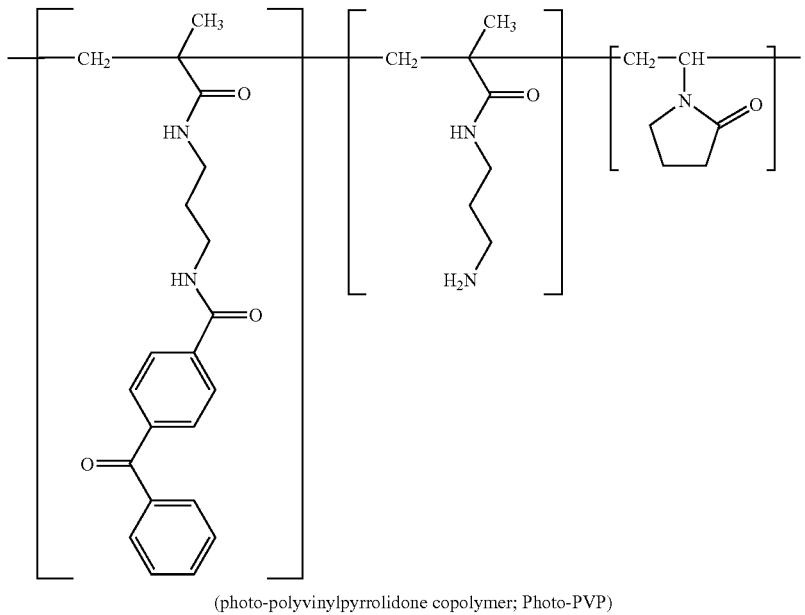
(photo-polyvinylpyrrolidone copolymer; Photo-PVP)
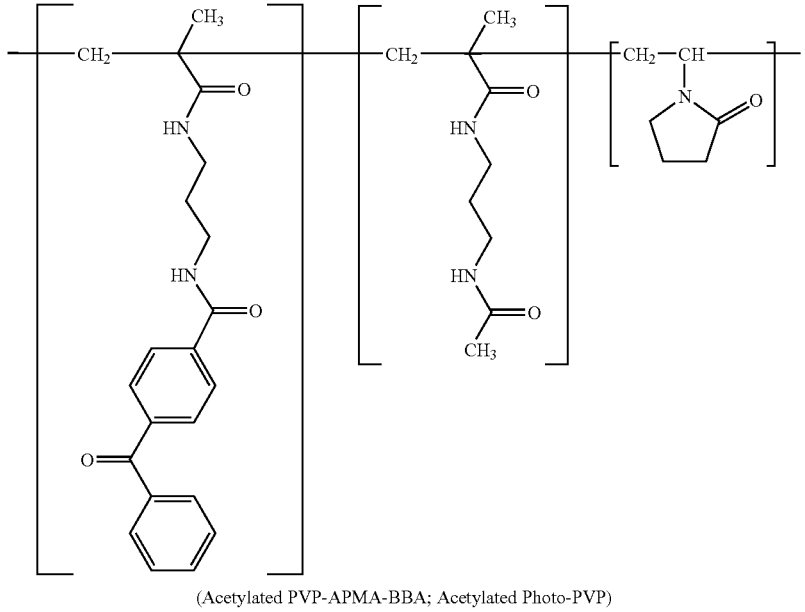
(Acetylated PVP-APMA-BBA; Acetylated Photo-PVP)

-continued

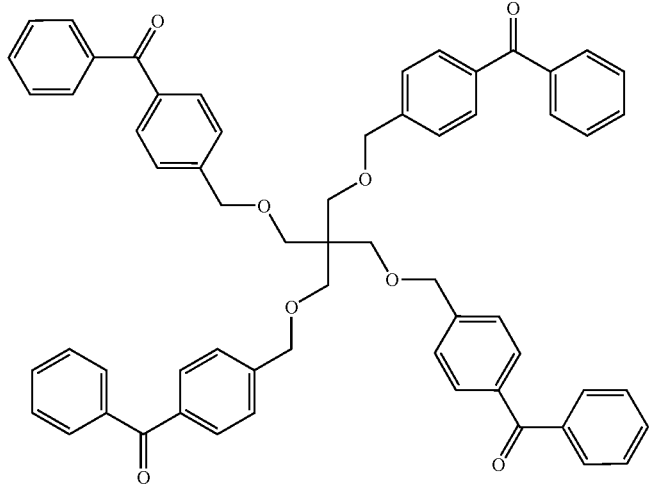

Compound IV (Tetrakis (4-benzoylbenzyl ether) of pentaerythritol (TBBE))

Spray Coating

The following spray coating procedure was followed in order to deposit a heparin-containing composition on the stents. The coating procedure was performed in order to provide stents with a desired amount of solids from the photo-heparin composition.

The parts were placed on a roller system such as that described in U.S. patent application Ser. No. 10/256,349 ("Advanced Coating Apparatus and Method," Chappa et al., filed Sep. 27, 2002). The device rotator included a pair of rollers suitable for holding the stent, the pair having first and second rollers arranged substantially parallel to each other and separated by a gap. The spray nozzle was operationally arranged to produce spray of a coating material directed at the gap and, when the device is not positioned on the pair of rollers, arranged so the majority of the spray was passed through the gap. In use, a heparin-containing composition was disposed on the device from the spray nozzle, and the majority of any spray that did not get deposited on the device was passed through the gap. The stent was then rotated by rotation of the rollers to position a different portion of the device for subsequent application of the heparin-containing composition. Coating was applied to the stent at a rate of 0.5 mL/min (or at a rate in the range of 0.03-0.1 mL/min as indicated). The spray nozzle utilized was an ultrasonic nozzle operated at a power of 0.6 W (unless otherwise noted), such as that commercially available from Sonotek (Ultrasonic spray coater) and described in U.S. patent application Ser. No. 10/256,349. The coating parameters were as follows. The spray nozzle moved over stents at a rate of 50-150 mm/sec. The spray head passed over the stent 10-120 times (Examples 1-5) or 150-320 times (Examples 7-13) (described as the number of "passes"; 2 passes equals 1 cycle), as indicated. The total number of passes was selected to provide a final coated weight of heparin in the range of 5-10 µg/stent, and a final heparin-containing layer weight in the range of 50-150 µg. Also, the stent was rotated during the spray coating process a sufficient number of times to provide a uniform coating on the surface (typically, the stent was rotated a minimum of 2 revolutions per coating application). In some cases, where indicated, a 20% speed pause was implemented after each cycle. The spray coatings were applied in a low humidity environment (less than 5% humidity). The coating solution was supplied from the spray nozzle at a pressure at 2 psi unless otherwise noted.

Heparin Activity Assay

The antithrombotic activity of heparin is due to its inhibition of thrombin, which is a protease that is known to participate in the clotting cascade. Heparin inhibits thrombin activity by first binding to antithrombin III (ATIII). The heparin/ATIII complex then binds to and inactivates thrombin, after which the heparin is released and can bind to another ATIII. The assay for inhibition of thrombin by immobilized heparin was conducted by measuring the cleavage of a chromogenic peptide substrate by thrombin.

Prior to performing the Heparin Activity Assay, coated stents were washed overnight (12-18 hours) to remove any unbound material from the coated stents. Coated stents were washed in $diH_2O$ or PBS at a temperature of about 37° C. on an orbital shaker (set for gentle agitation).

Each assay was conducted in 1 mL of PBS that contained 0.85 mg BSA (Sigma Chemical Co.), 10 mU human thrombin (Sigma Chemical Co.), 100 mU/mL ATIII (Baxter Biotech, Chicago, Ill.), and 0.17 µmole of the chromogenic thrombin substrate S-2238 (Kabi Pharmacia, Franklin, Ohio). To this assay solution was added either uncoated or heparin coated stents (to evaluate heparin activity on the membranes) or standard concentrations of heparin (to generate standard curves of heparin content versus absorbance). For standard curves, the amounts of heparin that were added ranged from 2.5 mU to 25 mU. The color generated, measured as absorbance at 405 nm, by thrombin mediated cleavage of the S-2238 was read using a spectrophotometer after 2 hours of incubation at 37° C. The absorbance was directly related to the activity of the thrombin and, thus, inversely related to the amount of activation of ATIII induced by the heparin in solution or immobilized on the surface of the substrate. Activity of surface bound heparin was calculated by comparing the absorbance values generated with the membranes to the absorbance values generated with known amounts of added heparin. Commercial preparations of heparin are commonly calibrated in USP units, 1 unit being defined as the quantity that prevents 1.0 mL of citrated sheep plasma from clotting for 1 h after the addition of 0.2 mL of 10 g/L $CaCl_2$ (see Majerus P W, et al. Anticoagulant, thrombolylic, and antiplatelet drugs. In: Hardman J G, Limbrid L E, eds., Goodman and Gilman's The pharmacological bases of therapeutics, 9th ed, New York: McGraw Hill, 1996:1341-6). Commercial preparations of heparin typically include the heparin activity of the preparation. In order to determine the heparin activity of a heparin coating described herein, the above assay can be performed and compared to a standard generated from a commercial preparation of heparin, based on the above definition of heparin activity.

For all examples, 1-7 stents had a surface area of 0.8757 $cm^2$.

Example 1

Coating composition premixtures containing pBMA (poly (butyl)methacrylate); and photo-heparin (Compound I) were prepared and coated on stainless steel stents, demonstrating that a medical article having a coating containing an adhesion polymer and having biocompatible properties can be prepared in a process that requires a minimum number of steps.

Solutions of pBMA at a concentration of 10 mg/ml in 90% THF, 10% $H_2O$, and a solution of pBMA at a concentration of 10 mg/ml in 100% THF was prepared. Solutions of photo-heparin at concentrations of 5 mg/ml and 10 mg/ml in 90% THF 10% $H_2O$, and a solution of photo-heparin at 50 mg/ml in $H_2O$ was prepared. For a control, a solution of heparin (non-photo) at 50 mg/ml in $H_2O$ was prepared. At these concentrations the pBMA and photo-heparin did not precipitate out of solution. The solutions of pBMA and photoheparin were mixed in order to prepare mixtures having the following concentrations of pBMA and photo-heparin:

(A) 5 mg/ml photo-heparin; 2.5 mg/ml pBMA
(B) 5 mg/ml photo-heparin; 10 mg/ml pBMA
(C) 5 mg/ml heparin (non-photo); 10 mg/ml pBMA The percentage of solvents in mixtures (A)-(C) was 90% THF, 10% $H_2O$.

Mixtures (A)-(C) were disposed on stents using the spray coating technique described herein. In some samples (1-B3/B4 and 1-C3/C4, see Table 1) the coated stents were subject to irradiation for 45 seconds at 6-8 mW/cm2 using a 324 nm filter. In other samples no irradiation was performed.

TABLE 1

| Sample No. | Irradiation after spray coating | Surface Characteristic | Heparin activity (mU/cm$^2$) |
|---|---|---|---|
| 1-A1 | Yes | Dewet | 29 |
| 1-A2 | Yes | Dewet | 17 |
| 1-B1 | Yes | Dewet | 26 |
| 1-B2 | Yes | Dewet | 27 |
| 1-B3 | No | Dewet | nr |
| 1-B4 | No | Dewet | nr |
| 1-C1 | Yes | Dewet | 6 |
| 1-C2 | Yes | Dewet | 2 |
| 1-C3 | No | Dewet | nr |
| 1-C4 | No | Dewet | nr | nr = not recorded

Heparin activity was shown on the surface of stents coated with pBMA and photoheparin (at two different concentrations (1-A1/A2 and 1-B1/B2) that were also subject to an irradiation step. Stents not receiving a dose of UV irradiation (1-B3/B4 and 1-C3/C4), or stents that received irradiation but had a coating that included non-photo heparin (1-C 1/C2) demonstrated little or no surface heparin activity.

Example 2

Coating composition premixtures containing pBMA, photo-heparin, and acetylated-photo-PVP (Compound III) were prepared and coated on stainless steel stents. The stents had coatings that demonstrated excellent biocompatibility properties.

A mixture of pBMA at a concentration of 5 mg/ml, photo-heparin at 2.5 mg/ml, and photo-polyvinylpyrrolidone at 0.25 mg/ml in 90% THF and 10% $H_2O$ was prepared (Table 2).

Stents were coated using the spray coating apparatus having a pair of rollers and an ultrasonic nozzle (as described herein) at rate of 0.03 ml/min, 20% speed, and 1 psi. 20-50 μg of mixture was coated onto each stent.

After the coating was performed the stents were: not subject to an irradiation step (2-A1/A2), subject to UV irradiation for 45 seconds at 6-8 mW/cm$^2$ using a 324 nm filter (2-A3/A4), or subject to UV irradiation in addition to receiving a top coat of photo-heparin (2-A5/A6). A heparin top coat was applied to the stents (50 mg/ml photo-heparin in $H_2O$ applied by spray coating and then irradiated for 45 seconds).

Results of heparin activity for the coated stents are shown in Table 2.

TABLE 2

| Sample No. | Irradiation after coating | Photo-heparin topcoat | Heparin activity (mU/cm$^2$) |
|---|---|---|---|
| 2-A1 | No | No | 0 |
| 2-A2 | No | No | 2 |
| 2-A3 | Yes | No | 42 |
| 2-A4 | Yes | No | 41 |
| 2-A5 | Yes | Yes | 41 |
| 2-A6 | Yes | Yes | 40 |

High levels of heparin activity were shown on the surface of stents coated with the pBMA/photo-heparin/photo-PVP mixture and that were also treated with UV irradiation (2-A3/A4 and A5/A6). Stents having high levels of heparin activity were able to be prepared (2-A3/A4) without a heparin topcoat (2-A5/A6). Coated stents not receiving a dose of UV irradiation (2-A1/A2) demonstrated little or no surface heparin activity.

Example 3

Coating composition premixtures containing photo-heparin and photo-PVP were prepared and subject to UV irradiation. The irradiated premixtures of photo-heparin and acetylated photo-PVP were then added to a solution of pBMA and the resulting mixtures were then coated on stents. Stents having surface heparin activity were able to be prepared without directly irradiating the stent surface.

In addition, the coating compositions were applied in an improved coating solution that included isopropanol alcohol.

A miscibility test was first performed to determine if isopropanol alcohol is suitable as a common liquid for preparing a mixture of pBMA, photo-heparin, and acetylated photo-PVP. pBMA was dissolved at a concentration of 10 mg/ml in 80% isopropanol (IPA), 20% THF. Photo-heparin was dissolved at a concentration of 10 mg/ml in 90% IPA, 10% $H_2O$. Acetylated photo-PVP was dissolved at a concentration of 10 mg/ml in 100% IPA. To 7 mls of EPA was added each 1 ml of the pBMA, photo-heparin, and acetylated photo-PVP solutions. The solution was slightly cloudy without any observable precipitate, demonstrating that isopropanol can be included as a liquid to improve properties of a coating mixture.

Stents having surface heparin activity were prepared without subjecting the coated stent to a treatment of UV irradiation as follows. First, premixtures of photo-heparin at a concentration of 7.5 mg/ml, and acetylated photo-PVP at 5.0 mg/ml in $H_2O$ were prepared and subject to UV irradiation for either 20 seconds (3-B1/B2) or 30 seconds (3-C1/C2) at 6-8 mW/cm$^2$. Non-irradiated mixtures of photo-heparin and acetylated photo-PVP were also prepared (3-A1/A2). The irradiated mixture was then combined with pBMA to give a coating mixture having 1 mg/ml pBMA, 0.75mg/ml photo-heparin, and 0.5 mg/ml photo-PVP in 88% IPA, 10% $H_2O$, 2% THF. The coatings were then spray coated onto stainless steel stents as described in Example 2 and then heparin activity was determined (results shown in Table 3).

TABLE 3

| Sample No. | Irradiation of photo-herparin/ photo-PVP premix | Irradiation after coating | Heparin activity (mU/cm$^2$) |
|---|---|---|---|
| 3-A1 | No | No | 3 |
| 3-A2 | No | No | 3 |
| 3-B1 | Yes, 20 sec | No | 7 |
| 3-B2 | Yes, 20 sec | No | 7 |
| 3-C1 | Yes, 30 sec | No | 7 |
| 3-C2 | Yes, 30 sec | No | 7 |

According to the results shown in Table 3, heparin activity on the surface of stents that had a coating that included an irradiated premixture of photo-heparin and acetylated photo-PVP (3-B1/B2 and 3-C1/C2) was more than two times the heparin activity as compared to stents having a coating wherein the photo-heparin and acetylated photo-PVP premixture was not irradiated (3-A1/A2).

Example 4

Stents were also prepared that included coatings as described in Example 3, but in addition included steps of treating the coated surface with UV and adding a topcoat of photoheparin following the initial coating. Both Parylene™-C and bare metal stents were able to be prepared having coatings with excellent heparin activity.

Coating mixtures as described above (used in the preparation of 3-A1/A2, 3-B1/B2, and 3-C1/C2 of Example 3) were disposed on Parlene-C stents as described and then treated with UV irradiation for one minute at 6-8 mW/cm$^2$. A topcoat of heparin was then added to the stents to complete the preparation of samples 4-A1/A2, 4-B1/B2, and 4-C1/C2, respectively.

TABLE 4

| Sample No. | Irradiation of photo-heparin/ photo-PVP premix | Irradiation after coating | Photo-heparin topcoat | Heparin activity (mU/cm$^2$) |
|---|---|---|---|---|
| 4-A1 | No | Yes | Yes | 46 |
| 4-A2 | No | Yes | Yes | 47 |
| 4-B1 | Yes, 20 sec | Yes | Yes | 49 |
| 4-B2 | Yes, 20 sec | Yes | Yes | 45 |
| 4-C1 | Yes, 30 sec | Yes | Yes | 46 |
| 4-C2 | Yes, 30 sec | Yes | Yes | 48 |

Coating mixtures that included different photo-PVP polymers (acetylated and non acetylated) and different concentrations of the photo-PVP polymers were prepared and used to coat bare metal stents. The following coating compositions were prepared:

(4-D1/D2) 1 mg/ml pBMA, 1 mg/ml photo-heparin, and 1 mg/ml acetylated photo-PVP in 90% IPA, 10% $H_2O$.

(4-E1/E2) 1 mg/ml pBMA, 1 mg/ml photo-heparin, and 1 mg/ml photo-PVP (non acetylated) in 90% IPA, 10% $H_2O$.

(4-F1/F2) 1 mg/ml pBMA, 1 mg/ml photo-heparin, and 0.2 mg/ml photo-PVP (non acetylated) in 90% IPA, 10% $H_2O$.

(4-G1/G2) 1 mg/ml pBMA, 1 mg/ml photo-heparin in 90% IPA, 10% $H_2O$.

Coating mixtures (K)-(M) were disposed on bare metal stents using spray coating and then treated with UV irradiation for one minute at 6-8 mW/cm$^2$. A topcoat of heparin (in 10 mg/ml in 80% EPA, 20% $H_2O$) was then added to the stents.

TABLE 5

| Sample No. | Irradiation after coating | Photo-heparin topcoat | Heparin activity (mU/cm$^2$) |
|---|---|---|---|
| 4-D1 | Yes | Yes | 45 |
| 4-D2 | Yes | Yes | 44 |
| 4-E1 | Yes | Yes | 46 |
| 4-E2 | Yes | Yes | 46 |
| 4-F1 | Yes | Yes | 45 |
| 4-F2 | Yes | Yes | 46 |
| 4-G1 | Yes | Yes | 29 |
| 4-G2 | Yes | Yes | 31 |

Results from Table 5 demonstrate that the coating composition and methods can provide bare metal stents with an excellent heparin surface activity and that different miscibility enhancers can be used to prepare surfaces having excellent heparin surface activity.

Example 5

Coating composition premixtures containing photo-heparin, photo-PVP, and pBMA are prepared and subject to UV irradiation. The irradiated premixtures of photo-heparin, photo-PVP, and pBMA are then coated on stents.

Stents having surface heparin activity are prepared without subjecting the coated stent to a treatment of UV irradiation as follows. First, premixtures of 1 mg/ml pBMA, 0.5 mg/ml photo-heparin, and 0.75 mg/ml photo-PVP in 90% IPA, 10% $H_2O$ are prepared and dried. The dried premixture is then irradiated and subject to UV irradiation. The coatings are then resuspended in IPA/$H_2O$ and then coated onto stainless steel stents as described in Example 2.

Example 6

Coating composition premixtures containing photo-collagen and pBMA were prepared and disposed on metal flats and then subject to UV irradiation. To determine collagen activity, a cell attachment assay was performed by incubating PA-1 cells with the coated flats and determining cell adherence. Very good collagen activity was achieved using premixtures of photo-collagen and pBMA.

Stainless steel flats (316 L; 1×3 cm) were coated using the ultrasonic spray coater as described herein using a grid type pattern to coat the flats. The following compositions were coated on the flats:

(6-A) 1 mg/ml pBMA in 90% IPA, 10% $H_2O$.

(6-B) 0.3 mg/ml photo-heparin in 90% IPA, 10% $H_2O$.

(6-C) 0.4 mg/ml pBMA, 0.3 mg/ml photo-collagen in 90% IPA, 10% $H_2O$.
(6-D) 1 mg/ml pBMA, 0.3 mg/ml photo-collagen in 90% IPA, 10% $H_2O$.
(6-E) 2 mg/ml pBMA, 0.3 mg/ml photo-collagen in 90% IPA, 10% $H_2O$.
(6-F) 4 mg/ml pBMA, 0.3 mg/ml photo-collagen in 90% EPA, 10% $H_2O$.
(6-G) 4 mg/ml pBMA, 0.3 mg/ml photo-collagen in 90% IPA, 10% $H_2O$.

Sample (6-F) was coated onto a metal flat having a pBMA base coat. Sample (6-G) was coated onto a metal flat having a Parylene™ C base coat. Tissue culture polystyrene and photocollagen on polystyrene (details) were used as controls.

Controls included uncoated tissue culture polystyrene (6-H) and photocollagen immobilized on polystyrene (6-I). Photocollagen was diluted in 12 mM HCl to 200 ug/ml and incubated in wells of a tissue culture plate for one hour at room temperature; the well was then illuminated for 90 seconds in a refrigerated illumination chamber with a Dimax 365 nm lamp and then washed with PBS). The coated metal flats were then mounted in the wells.

MEM (Modified Eagles Media) was added to each well (0.5 ml) and incubated at least 30 minutes at 37° C. and 5% $CO_2$. PA-1 cells were added to each well at a concentration of 150,000 cells/ml at 0.5 ml per well in MEM (Modified Eagles Media)+2% BSA and incubated 90 minutes at 37° C. and 5% $CO_2$. Media was then carefully removed from the wells and the wells were gently rinsed with 1 ml of MEM to remove unattached cells.

A chromogenic assay was performed to determine the number of cells adhered to the coated metal flats. A solution of MTT at 5 mg/ml in PBS was prepared and sterile filtered. A mixture of media/MTT was prepared by adding 5 ml of fresh media to 1.2 ml of the MTT preparation. After the cells were rinsed 0.5 ml of the media/MTT mixture was added to each well and then incubated for 90 minutes at 37° C. and 5% $CO_2$. The media/MTT mixture was then removed with the flats and transferred to new wells. The dye was solubilized with 0.5 ml of 0.04 N HCl/isopropanol and 0.12 ml 3% $SDS/H_2O$. Plates were shaken at room temperature at 100 rmp until the dye was completely solubilized and uniformly mixed. 200 ul aliquot samples were transferred in duplicate into 96 well plates and the absorbance of the solution at 570 nm was determined.

Results are shown in Table 6.

TABLE 6

| Sample No. | A570 |
|---|---|
| 6-A | 0.020 |
| 6-B | 0.025 |
| 6-C | 0.040 |
| 6-D | 0.080 |
| 6-E | 0.050 |
| 6-F | 0.060 |
| 6-G | 0.055 |
| 6-H | 0.015 |
| 6-I | 0.135 |

As shown in Table 6, substrates coated with mixtures of pBMA and photocollagen gave surfaces that allowed for greater cell adhesion than the pBMA-coated or photocollagen surfaces alone. In addition, mixtures of pBMA and photocollagen were able to coat surfaces already having a layer of either pBMA or photocollagen alone and provide these surfaces with very good cell adhesive properties. Surfaces coated with a mixture of pBMA at 1 mg/ml and photocollagen at 0.3 mg/ml had particularly good cell adhesive properties.

Substrates (Examples 7-13)

18 mm×6 cell cobalt chromium stents having a surface area of 1.0 $cm^2$ were used as substrates, unless otherwise indicated, for coating procedures.

The cobalt chromium stents were prepared for coating by soaking in a cleansing solution of ENPREP (ENTHOME-OMI, Inc.) at a concentration of 60 mg/mL in DI water at a temperature of approximately 80° C. for approximately 1 hour. After soaking, the stents were rinsed twice in distilled water for about 10 seconds each and then rinsed with IPA twice for 10 seconds each. After rinsing, the stents were immersed in a silane solution as indicated below.

Coating Materials and Method for Forming Coated Layers (Examples 7-13)

For purposes of discussion in the Examples 7-13, the following materials were used to form coated layers on the surface of the stents unless otherwise indicated:

(I) Silane layer. A silane layer was formed on the stents by immersing the (bare metal) cleansed cobalt chromium stents in a solution of 0.5% (w/v) γ-methacryloxypropyltrimethylsilane in a mixture of IPA/water at room temperature for approximately 1 hour with shaking on an orbital shaker. After silane treatment, the stents were briefly rinsed in IPA and then baked in an oven at a temperature of 100° C. for approximately 1 hour.

(II) Parylene™ C layer. To form the Parylene™ layer, the silane-coated stents by were placed in a Parylene™ coating reactor (PDS 2010 LABCOTER™ 2, Specialty Coating Systems, Indianapolis, Ind.) and coated with Parylene™ C (Specialty Coating Systems, Indianapolis, Ind.) by following the operating instructions for the LABCOTER™ system. The resulting Parylene™ C coating was approximately 1-2 μm thickness.

(III) pBMA/pEVA/rapamycin layer. For preparing the pBMA/pEVA/rapamycin layer, a mixture of pEVA (33 weight percent vinyl acetate; Aldrich Chemical, Milwaukee, Wis.) at a concentration of 1.67 mg/ml; pBMA (337,000 average molecular weight; Aldrich Chemical, Milwaukee, Wis.) at a concentration of 1.67 mg/ml; and rapamycin (Sirolimus, Wyeth) at a concentration of 1.67 mg/ml, was prepared in THF. The pBMA/pEVA/rapamycin solution was sprayed onto the Parylene™ C treated stents using an IVEK sprayer (IVEK Dispenser 2000, IVEK Corp., North Springfield, Vt.) having a nozzle with a 1.0 mm (0.04 inch) diameter orifice and pressurized at 421.84 $g/cm^2$ (6 psi). The distance from the nozzle to the stent surface during coating application was in the range of 5 cm to 5.5 cm. A coating application consisted of spraying 40 μL of the coating solution back and forth on the stent for 7 seconds. The spraying process of the coating was repeated until a desired amount of drug was present on the stents. The coating compositions on the stent were dried by evaporation of solvent, approximately 8-10 hours, at room temperature (approximately 20° C. to 22° C.). After drying, the coated wires were re-weighed. From this weight, the mass of the coating was calculated, which in turn permitted the mass of the coated polymer(s) and bioactive agent to be determined. The compositional details are summarized as a ratio of the weight percentages of the solid components in the composition.

(IV) pBMA layer. For preparation of the pBMA layer, a solution pBMA (337,000 average molecular weight; Aldrich Chemical, Milwaukee, Wis.) at a concentration of 2.5 mg/ml; was prepared in THF. The pBMA solution was sprayed onto the coated stents using an IVEK sprayer (IVEK Dispenser 2000, IVEK Corp., North Springfield, Vt.) mounting a nozzle with a 1.0 mm (0.04 inch) diameter orifice and pressurized at 421.84 g/cm$^2$ (6 psi). The distance from the nozzle to the stent surface during coating application was in the range of 5 cm to 5.5 cm. A coating application consisted of spraying 40 μL of the coating solution back and forth on the stent for 7 seconds. The spraying process of the coating was repeated until a desired amount of drug was present on the stents. The coating compositions on the stent were dried by evaporation of solvent, approximately 8-10 hours, at room temperature (approximately 20° C. to 22° C.). After drying, the coated wires were re-weighed.

(V) Heparin-containing layer. Coating compositions were prepared that consisted of various combinations of some or all the following materials:

pBMA
photo-PVP (Compound II)
photo-heparin (Compound I) or heparin
photo-crosslinker Preparation of the pBMA/photo-PVP/photo-heparin mixture in a ternary solvent system (THF/IPA/H$_2$O) was carried out in a sequential manner. The following solutions were prepared at room temperature:

(i) pBMA at 50 mg/mL in THF
(ii) photo-PVP at 50 mg/mL in IPA
(iii) photo-heparin at 50 mg/mL in H$_2$O In order to prepare a 10 mL of a heparin coating solution containing: pBMA (5.0 mg/mL)/photo-PVP (0.3125 mg/mL)/photo-heparin (0.625 mg/mL) in a final solution of 80% THF/5% IPA/15% H$_2$O, the following procedure was performed.

Solution (i) was diluted in THF by adding 1 mL of (i) to a mixture of 7 mL of THF and 0.4375 mL of IPA. Next, a photo-PVP/photo-heparin mixture was prepared by adding 62.5 μl of solution (ii) and 125 μl of solution (iii) into 1.375 mL of H$_2$O. (Optionally, photo-PVP and photo-heparin can be individually dissolved in water and added to the mixture). The mixture of (ii) and (iii) was then shaken briefly at room temperature. The photo-PVP/photo-heparin mixture was then added to the pBMA solution. Various heparin coating solutions were prepared in this sequential manner having the following solvents present in these ranges:

THF: 20% -80% final
IPA: 5% -75% final
H$_2$O: 5% -20% final

Preparation of pBMA/photo-PVP/photo-heparin mixtures in a binary solvent system (IPA/H$_2$O) or (THF/H$_2$O) was carried out in a sequential manner by first preparing solution of pBMA in IPA or THF, and then adding a mixture of photo-PVP and photo-heparin dissolved in water to the pBMA solution.

In some cases, coating compositions were prepared by substituting heparin (not photo-derivitized) for photo-heparin.

Rapamycin Analysis—Drug Content Method by HPLC

Rapamycin content and quality from coated stent samples were analyzed by immersing the (18 mm) coated stents into a glass test tube filled with 5 mL acetonitrile, which dissolves coated material, including rapamycin, from the cobalt chromium stent surface. The tube was capped and shaken for 30-45 minutes using a mechanical shaker. After shaking, a portion of the acetonitrile sample (having the eluted rapamycin) was sampled by HPLC using the following parameters:

Column: Supelco Hypersil BDS C18, 5 μm, 4.6×250
Temp: 40° C.

Mobile phase: 1,4-dioxane:water (3:2 v:v; mixed and degassed by H$_2$ sparging)
Flow rate: 0.8±0.1 mL/min
Detection λ: 225 nm
Injection volume: 25 μL
Run time: 40 min.

The HPLC column was equilibrated with the mobile phase solution (1,4-dioxane:water) and tested using a rapamycin standard, which produces peaks for the rapamycin isomers (B and C) and seco-rapamycin peaks. In order to determine the amount of rapamycin (μg) content in the stent coating, at least five rapamycin standard solutions were run and an average total peak area for the B and C isomers were determined ($A_{standard}$) in addition to the purity of the standards (purity factor (PF)). Next, test samples (ACN with rapamycin eluted from coated stents) were run on the HPLC and average total peak areas for the B and C isomers were determined ($A_{test}$). $W_{standard}$ is the weight of the rapamycin reference standard in mg and DF is the dilution factor of the test sample. Following HPLC and rapamycin peak analysis, the following calculation was performed to determine the amount of rapamycin (μg) eluted from the stent:

$$((A_{test} \times W_{standard} \times DF \times PF)/A_{standard})$$

Purity of the eluted rapamycin was determined by determining the peak area of the impurity peak(s) for the test samples ($A_{impurity\text{-}test}$) and calculating based on this formula (percent impurity):

$$((A_{impurity\text{-}test} \times 100)/A_{standard})$$

Rapamycin Analysis—Drug Dissolusion Method

Drug dissolution (elution of rapamycin from the coating) was performed using a Sotax CE7 Smart/Agilent 8453 UV Spectrophotometer Dissolution System. The following parameters were applied for the assessing the amount of rapamycin eluted from the coated stents.

Dissolution Medium: 2% SLS
Temperature: 37° C.
Flowrate: 16 ml/min
Sampling Interval: 15 minutes (1$^{st}$ 3 hours)
Sampling Interval: 60 minutes (after first 3 hours–24 hours)
12 mm Cell (stents are placed here) 7 individual cells per run
279, or 292 nm Rapamycin peak used for calculations Example 7

Heparin coating compositions containing pBMA/photo-PVP/photo-heparin mixtures (samples 7-C1 to 7-C14) or pBMA/photo-heparin mixtures (samples 7-B1 to 7-B8) in ternary or binary solvent systems were spray coated onto stents having a pre-coating containing all of the following coated layers: (I) silane layer, (II) Parylene™ layer, (III) pBMA/pEVA/rapamycin layer, and (IV) pBMA layer (as described herein).

The heparin compositions were spray coated using the ultrasonic coating apparatus onto pre-coated stents to provide a target coating weight (the heparin-containing layer) of approximately 100 μg, and within the range of 50 μg to 150 μg.

The concentrations of pBMA, photo-PVP, and photo-heparin in the heparin-containing layer, as well as the percentages of THF, IPA, and H$_2$O for all of the coating compositions are described in Table 7.

Mixtures were disposed on stents using the spray coating technique described herein. In some samples the coated stents were subject to irradiation for 60 seconds at 1 mW/cm$^2$ using a 407 run center wavelength filter (Edmund).

A mixture of pBMA/photo-PVP was used as a heparin activity control (samples 7-A1 and 7-A2).

TABLE 7

| Sample No. | Coating Composition | | | | | | Heparin activity (mU/cm²) |
|---|---|---|---|---|---|---|---|
| | Reagent (mg/mL) | | | Solvent (%) | | | |
| | pBMA | photo-PVP | Photo-heparin | THF | IPA | H₂O | |
| 7-A1 | 5 | 2.5 | (—) | 90 | 10 | (—) | 4 |
| 7-A2 | 5 | 2.5 | (—) | 90 | 10 | (—) | 4 |
| 7-B1 | 5 | (—) | 5 | 90 | (—) | 10 | 8 |
| 7-B2 | 5 | (—) | 5 | 90 | (—) | 10 | 13 |
| 7-B3 | 2.5 | (—) | 5 | 90 | (—) | 10 | 7 |
| 7-B4 | 2.5 | (—) | 5 | 90 | (—) | 10 | 12 |
| 7-B5 | 5 | (—) | 5 | 90 | (—) | 10 | 9 |
| 7-B6 | 5 | (—) | 5 | 90 | (—) | 10 | 10 |
| 7-B7 | 2.5 | (—) | 2.5 | 90 | (—) | 10 | 6 |
| 7-B8 | 2.5 | (—) | 2.5 | 90 | (—) | 10 | 11 |
| 7-C1 | 5 | 1.25 | 2.5 | 65 | 10 | 25 | 64 |
| 7-C2 | 5 | 1.25 | 2.5 | 65 | 10 | 25 | 67 |
| 7-C3 | 5 | 0.3125 | 1.25 | 80 | 5 | 15 | 66 |
| 7-C4 | 5 | 0.3125 | 1.25 | 80 | 5 | 15 | 67 |
| 7-C5 | 5 | 0.3125 | 0.625 | 80 | 5 | 15 | 67 |
| 7-C6 | 5 | 0.3125 | 0.625 | 80 | 5 | 15 | 64 |
| 7-C7 | 2.25 | 2.5 | 4.5 | 72 | 18 | 10 | 78 |
| 7-C8 | 2.25 | 2.5 | 4.5 | 72 | 18 | 10 | 66 |
| 7-C9 | 2.5 | 1.25 | 1.25 | 70 | 10 | 20 | 62 |
| 7-C10 | 2.5 | 1.25 | 1.25 | 70 | 10 | 20 | 70 |
| 7-C11 | 2.5 | 0.94 | 2.5 | 75 | 7.5 | 17.5 | 59 |
| 7-C12 | 2.5 | 0.94 | 2.5 | 75 | 7.5 | 17.5 | 73 |
| 7-C13 | 2.5 | 0.3125 | 1.25 | 80 | 5 | 15 | 60 |
| 7-C14 | 2.5 | 0.3125 | 1.25 | 80 | 5 | 15 | 61 |

High levels of heparin activity were shown on the surface of stents coated with pBMA/photo-PVP/photo-heparin mixtures. Stents coated with pBMA/photo-heparin mixtures (no photo-PVP) had very low levels of heparin activity.

Example 8

Various heparin coating compositions containing pBMA/photo-PVP/photo-heparin mixtures in ternary solvent systems having varying THF/IPA/H₂O ratios (samples J-K) were spray coated onto pre-coated stents. The pre-coated stents had a pre-coating containing all of the following coated layers: (I) silane layer (II) Parylene™ layer, (III) pBMA/pEVA/rapamycin layer, and (IV) pBMA layer, as indicated above. One sample utilized an IPA/H₂O binary solvent system.

The compositions were spray coated onto the stents to provide a coating weight (for the heparin-containing layer) of approximately 100 μg, and in the range of 50 μg to 150 μg.

The concentrations of pBMA, photo-PVP, and photo-heparin, as well as the percentages of THF, IPA, and H₂O for all of the coating compositions are described in Table 8.

Mixtures were disposed on stents using the spray coating technique described herein. In some samples the coated stents were subject to irradiation for 60 seconds at 1 mW/cm² using a 407 nm center wavelength filter (Edmund).

TABLE 8

| Sample No. | Coating Composition | | | | | | Heparin activity (mU/cm²) |
|---|---|---|---|---|---|---|---|
| | Reagent (mg/mL) | | | Solvent (%) | | | |
| | pBMA | photo-PVP | Photo-heparin | THF | IPA | H₂O | |
| 8-A1 | 5 | 0.625 | 0.625 | (—) | 95 | 5 | 18 |
| 8-A2 | 5 | 0.625 | 0.625 | (—) | 95 | 5 | 20 |
| 8-A3 | 5 | 0.625 | 0.625 | (—) | 95 | 5 | 11 |
| 8-B1 | 5 | 0.3125 | 0.625 | 80 | 5 | 15 | 31 |
| 8-B2 | 5 | 0.3125 | 0.625 | 80 | 5 | 15 | 35 |
| 8-B3 | 5 | 0.3125 | 0.625 | 80 | 5 | 15 | 35 |
| 8-C1 | 5 | 0.3125 | 0.625 | 70 | 15 | 15 | 34 |
| 8-C2 | 5 | 0.3125 | 0.625 | 70 | 15 | 15 | 37 |
| 8-D1 | 5 | 0.3125 | 0.625 | 60 | 25 | 15 | 40 |
| 8-D2 | 5 | 0.3125 | 0.625 | 60 | 25 | 15 | 39 |
| 8-E1 | 5 | 0.3125 | 0.625 | 50 | 35 | 15 | 34 |
| 8-E2 | 5 | 0.3125 | 0.625 | 50 | 35 | 15 | 32 |
| 8-F1 | 5 | 0.3125 | 0.625 | 40 | 50 | 10 | 25 |
| 8-G2 | 5 | 0.3125 | 0.625 | 40 | 50 | 10 | 25 |
| 8-G3 | 5 | 0.3125 | 0.625 | 40 | 50 | 10 | 24 |
| 8-G4 | 5 | 0.3125 | 0.625 | 40 | 50 | 10 | 25 |
| 8-H1 | 5 | 0.3125 | 0.625 | 30 | 65 | 5 | 17 |
| 8-H2 | 5 | 0.3125 | 0.625 | 30 | 65 | 5 | 16 |
| 8-I1 | 5 | 0.3125 | 0.625 | 20 | 75 | 5 | 16 |
| 8-I2 | 5 | 0.3125 | 0.625 | 20 | 75 | 5 | 18 |

As shown in table 8, heparin activity improved upon increasing amounts of THF or H₂O in the coating compositions.

Example 9

Stents coated with pBMA/photo-PVP/photo-heparin compositions in different binary or ternary solvent systems were tested for durability using expansion testing, or expansion in combination with incubation in serum. In some cases the pBMA/photo-PVP/photo-heparin compositions were prepared by including a photoactivatable crosslinking agent (4,5-bis(4-benzoylphenylmethyleneoxy)benzene-1,3-disulfonic acid dipotassium salt (DBDS), as described in U.S. Pat.

No. 6,669,994). The heparin compositions were coated on stents having a pre-coating containing all of the following coated layers: (I) silane layer (II) Parylene™ layer, (III) pBMA/pEVA/rapamycin layer, and (IV) pBMA layer, as indicated above.

The amounts of components present in the heparin-containing compositions is indicated in Table 9.

TABLE 9

| | Coating Composition | | | | | |
|---|---|---|---|---|---|---|
| | Reagent (mg/mL) | | | | | |
| Sample set | pBMA | photo-PVP | photo-heparin | Photo-X-linker | Solvent (%) | | |
| | | | | | THF | IPA | H$_2$O |
| 9-(A1-A9) | 5 | 0.625 | 0.625 | (—) | (—) | 98.75 | 1.25 |
| 9-(B1-B8) | 5 | 0.625 | 0.625 | 0.1875 | (—) | 95 | 5 |
| 9-(C1-C9) | 5 | 0.625 | 0.625 | (—) | 80 | 5 | 15 |
| 9-(D1-D9) | 5 | 0.3125 | 1.25 | (—) | 80 | 5 | 15 |

In order to provide an equal amount of coating composition to the stents, sample sets 9-(A1-A9) and 9-(B1-B8) were subject to 75 cycles of spray coating, whereas sample sets 9-(C1-C9) and 9-(B1-B8) were subject to 160 cycles.

Sets A, B, C, and D of coated stents were then subject to durability testing. In one aspect durability testing was carried out by mechanical challenge by a balloon expansion process. The balloon expansion process was performed by hand crimping the stent down on an appropriately sized balloon in a 37° C. water bath and then expanding the balloon. In some cases stents were placed in Bovine Serum (Invitrogen Life Technologies) contained in a glass vial and shaken at 37° C. for the period of time as indicated in Table 10.

TABLE 10

| | Heparin Activity (mU/cm) | | | |
|---|---|---|---|---|
| Sample Nos. | 9-(A1-A9) | 9-(B1-B8) | 9-(C1-C9) | 9-(D1-D9) |
| 1 - control | 11 | 15 | 35 | 41 |
| 2 - control | 14 | 13 | 29 | 33 |
| 3 - balloon expanded | 10 | 12 | 34 | 35 |
| 4 - balloon expanded | 10 | 9 | 36 | 32 |
| 5 - balloon expanded + 1 day serum treatment | 9 | 10 | 31 | 33 |
| 6 - balloon expanded + 2 days serum treatment | 5 | 7 | 30 | 36 |
| 7 - balloon expanded + 3 days serum treatment | 4 | 7 | 30 | 29 |
| 8 - balloon expanded + 1 day serum treatment + detergent wash | 10 | 11 | 33 | 38 |
| 9 - balloon expanded + 1 day serum treatment + detergent wash | 11 | (—) | 33 | 28 |

As seen in the examples, sets 9-(C1-C9) and 9-(D1-D9) provided stents that maintained excellent heparin activity after mechanical challenge. Sets 9-(C1-C9) and 9-(D1-D9) were prepared with a solvent system that included THF.

Example 10

The content and quality of rapamycin from stents having a pBMA/photo-PVP/photo-heparin and pBMA/photo-heparin coatings were tested. These heparin-containing coatings were formed on stents having a pre-coating containing the following coated layers: (I) silane layer (II) Parylene™ layer, (III) pBMA/pEVA/rapamycin layer, and (IV) pBMA layer, as indicated above.

The pBMA/pEVA/rapamycin layer contained approximately 125-140 μg of rapamycin and in a total layer weight of about 450-510 μg.

The heparin coatings were spray coated onto the stents to provide a coating weight (for the heparin-containing layer) of approximately 100 μg, and in the range of 50 μg to 150 μg.

The coatings were dissolved in acetonitrile and rapamycin was analyzed from the dissolved coatings using the HPLC procedures described herein. In this Example, rapamycin was not eluted from the coatings but rather, the coatings were dissolved and rapamycin analyzed from the dissolved coatings.

TABLE 11

| | Coating Composition | | | | | | | |
|---|---|---|---|---|---|---|---|---|
| | Reagent (mg/mL) | | | Solvent (%) | | | % Recovery | % Area |
| Sample No. | PBMA | photo-PVP | photo-heparin | THF | IPA | H$_2$O | | |
| 10-A1 | 5 | 1.25 | 2.5 | 65 | 10 | 25 | 83 | 97.9 |
| 10-B1 | 2.5 | 1.25 | 1.25 | 70 | 10 | 20 | 86 | 97.7 |
| 10-C1 | 2.5 | 0.94 | 2.5 | 75 | 7.5 | 17.5 | 82 | 96.3 |
| 10-D1 | 2.25 | 4.5 | 2.5 | 72 | 18 | 10 | 82 | 96.3 |
| 10-E1 | 5 | (—) | 2.5 | 90 | (—) | 10 | 82 | 96.1 |
| 10-F1 | 2.5 | (—) | 2.5 | 90 | (—) | 10 | 82 | 97.2 |
| 10-G1 | 2.5 | (—) | 5 | 90 | (—) | 10 | 83 | 96.4 |
| 10-H1 | 5 | (—) | 5 | 90 | (—) | 10 | 83 | 97.9 |
| 10-I1 | 5 | 0.3125 | 0.625 | 80 | 5 | 15 | 80 | 94.7 |
| 10-J1 | 5 | 0.3125 | 1.25 | 80 | 5 | 15 | 83 | 96.6 |
| 10-K1 | 2.5 | 0.3125 | 1.25 | 80 | 5 | 15 | 80 | 97.6 |
| Cont 1 | (—) | (—) | (—) | (—) | (—) | (—) | 90 | 99.2 |
| Cont 2 | (—) | (—) | (—) | (—) | (—) | (—) | 90 | 98 |
| 10-B2 | 2.5 | 1.25 | 1.25 | 70 | 10 | 20 | 82 | 96.3 |
| 10-C2 | 2.5 | 0.94 | 2.5 | 75 | 7.5 | 17.5 | 85 | 95.8 |
| 10-D2 | 2.25 | 4.5 | 2.5 | 72 | 18 | 10 | 82 | 96.7 |
| 10-E2 | 5 | (—) | 2.5 | 90 | (—) | 10 | 80 | 96.4 |
| 10-F2 | 2.5 | (—) | 2.5 | 90 | (—) | 10 | 82 | 97.2 |
| 10-G2 | 2.5 | (—) | 5 | 90 | (—) | 10 | 79 | 98 |
| 10-H2 | 5 | (—) | 5 | 90 | (—) | 10 | 83 | 97.4 |
| 10-I2 | 5 | 0.3125 | 0.625 | 80 | 5 | 15 | 80 | 97.7 |
| 10-J2 | 5 | 0.3125 | 1.25 | 80 | 5 | 15 | 85 | 96.6 |
| 10-K2 | 2.5 | 0.3125 | 1.25 | 80 | 5 | 15 | 82 | 96.5 |

As seen from Table 11 rapamycin was recovered from the coatings at a good recovery percentage. In control samples (no photo-heparin-containing layer) 90% of the drug was recovered from the stent. None of the stents tested displayed a loss of rapamycin recovery of greater than 12.3% ([Cont 1-(10-I2)]/Cont 1; 90-79/90). None of the stents having a pBMA/photo-heparin/photo-PVP coating displayed a loss of rapamycin recovery of greater than 11.2% ([Cont 1-(10-I2)]/Cont 1). On average the loss of rapamycin recovery for stents having a pBMA/photo-heparin/photo-PVP layer was 8.4% ([90-82.46(ave)]/90).

As shown by chromatography analysis, the rapamycin recovered from the stents having a photo-heparin-containing layer, on average, had a very high level of purity. For control samples the % area as assessed by HPLC analysis was average of 98.6%. For stents having the pBMA/photo-heparin layer the loss in purity was only in the range of 0.61% to 2.5%.

For stents having the pBMA/photo-heparin layer the loss in purity was only in the range of 0.61% to 3.95%.

Example 11

The elution of rapamycin from stents either having or lacking a pBMA intermediate layer in combination with the pBMA/photo-PVP/photo-heparin layer were tested. Heparin-containing coatings were formed on stents having a pre-coating containing the following coated layers: (I) silane layer (II) Parylene™ layer, (III) pBMA/pEVA/rapamycin layer, and, when indicated, a (IV) pBMA layer.

This coating was applied and the drug layer was formed having an amount of rapamycin in the drug layer in the range of 153-169 µg.

Various amounts of heparin composition were deposited on the stent. The heparin coatings were spray coated onto the stents to provide a theoretical amount of heparin as indicated in Table 12.

Rapamycin was eluted by a Sotax method (described herein) over a period of 24 hours. After 24 hours the amount of rapamycin eluted from the stent (and dissolved in solution was determined).

In the samples, the pBMA/pEVA/rapamycin was formed having an amount of rapamycin in the range of 115-145 µg.

The coatings were dissolved in acetonitrile and rapamycin was analyzed from the dissolved coatings using the HPLC procedures described herein.

The stents were irradiated using the following conditions:
12-A1: Standard filter, UV 60 seconds at 0.8-1.2 mW/cm$^2$
12-A2: Standard filter, UV 30 seconds at 0.8-1.2 mW/cm$^2$
12-B1: 324 nm filter, UV 60 seconds at 2.0 mW/cm$^2$
12-B2: 324 nm filter, UV 30 seconds at 2.0 mW/cm$^2$
12-C1: BG-38 filter, UV 60 seconds at 1 mW/cm$^2$
12-C2: BG-38 filter, UV 30 seconds at 1 mW/cm$^2$
12-C3: BG-38 filter, UV 15 seconds at 1 mW/cm$^2$
12-D1: Opto-Sigma 077-3550, UV 60 seconds at 1.1 mW/cm$^2$
12-D2: Opto-Sigma 077-3550, UV 30 seconds at 1.1 mW/cm$^2$
12-E1: Opto-Sigma 077-3440, UV 30 seconds at 1.1 mW/cm$^2$ Measurement are made from a radiometer from International Light with a 335 filter (filter out UV outside of 330-340 nm wavelength)

The results from the samples shows the average percent recovery from a group of stents prepared and irradiated in the same manner.

TABLE 12

| Sample No. | pBMA inter. Coat | Heparin Coating Composition | | | | | | µg heparin | % rapa dissolv. |
|---|---|---|---|---|---|---|---|---|---|
| | | Reagent (mg/mL) | | | Solvent (%) | | | | |
| | | pBMA | photo-PVP | Photo-heparin | THF | IPA | H$_2$O | | |
| 11-A | No  | 5 | 1.25   | 2.5  | 65 | 10  | 25 | 18 | 82 |
| 11-B | Yes | 5 | 1.25   | 2.5  | 65 | 10  | 25 | 16 | 60 |
| 11-C | No  | 5 | 0.3125 | 1.25 | 80 | 5   | 15 | 13 | 79 |
| 11-D | Yes | 5 | 0.3125 | 1.25 | 80 | 5   | 15 | 10 | 52 |
| 11-E | No  | (—) | (—) | (—) | (—) | (—) | (—) | 0 | 83 |
| 11-F | Yes | (—) | (—) | (—) | (—) | (—) | (—) | 0 | 52 |

As seen from the control examples in Table 12 the presence of the pBMA intermediate layer caused a decrease in the amount of rapamycin eluted from the coated stents. However, the presence of the heparin-containing layer did not significantly affect the amount of rapamycin eluted from the coated stents.

Example 12

The content and quality of rapamycin in present in coatings from stents having heparin-containing coatings was tested following irradiation of the stents with UV through various filters. This test was performed to determine the effect of different types of filters on drug elution. Filter A (Edmunds Optics, 407 nm maximum transmittance), Filter B (324 nm cut-off filter), Filter C (BG-38, 470 nm maximum transmittance), and Filter D (Opto-Sigma 077-3550; colored Glass filter maximum transmittance at 500 nm), and Filter E (Opto-Sigma 077-3440 Colored Glass filter; maximum transmittance 400 nm) were used. Filters D and E have particularly low transmittance below 300 nm.

The stents were prepared, as indicated above, were (I) silane-treated and had a (II) Parylene™ base layer, (III) a pBMA/pEVA/rapamycin layer, (IV) a pBMA layer, and (V) a pBMA/photo-heparin/photo-PVP (as indicated in Table 13).

TABLE 13

| Filter/ UV | Heparin Coating Composition | | | | | | % Recovery |
|---|---|---|---|---|---|---|---|
| | Reagent (mg/mL) | | | Solvent (%) | | | |
| | pBMA | photo-PVP | Photo-heparin | THF | IPA | H$_2$O | |
| 12-A1 | 5 | 0.625  | 0.625 | 50    | 40   | 10 | 79.9 |
| 12-A2 | 5 | 0.625  | 0.625 | 50    | 40   | 10 | 85.4 |
| 12-B1 | 5 | 0.625  | 0.625 | 50    | 40   | 10 | 85.0 |
| 12-B2 | 5 | 0.625  | 0.625 | 50    | 40   | 10 | 84.4 |
| (—)   | 5 | 0.625  | 0.625 | 50    | 40   | 10 | 85.6 |
| 12-C1 | 5 | 0.625  | 0.625 | 50    | 40   | 10 | 84.1 |
| 12-C2 | 5 | 0.625  | 0.625 | 50    | 40   | 10 | 85.6 |
| 12-C1 | 5 | 0.3125 | 0.625 | 88.75 | 0.25 | 11 | 89.9 |
| 12-C2 | 5 | 0.3125 | 0.625 | 88.75 | 0.25 | 11 | 87.1 |
| 12-C3 | 5 | 0.3125 | 0.625 | 88.75 | 0.25 | 11 | 84.5 |
| 12-D1 | 5 | 0.3125 | 0.625 | 88.75 | 0.25 | 11 | 78.1 |
| 12-D2 | 5 | 0.3125 | 0.625 | 88.75 | 0.25 | 11 | 81.1 |
| 12-E1 | 5 | 0.3125 | 0.625 | 88.75 | 0.25 | 11 | 83.0 |
| (—)   | (—) | (—) | (—) | (—) | (—) | (—) | 83.9 |

Example 13

Heparin activity was tested on the surface of stents that were coated with various heparin-containing compositions, wherein the compositions were subject to irradiation either before or after the compositions were spray coated onto the surface of the stents.

The stents prepared, as indicated above, were (I) silane-treated and had a (II) Parylene™ base layer, (III) a pBMA/pEVA/rapamycin layer, (IV) a pBMA layer, and (V) a pBMA/photo-heparin/photo-PVP (as indicated in Table 14).

Pre-irradiation was performed by subjecting the heparin-containing composition to UV (non-filtered) for 2-4 times irradiation for 99 seconds per time.

Post-irradiation was performed by subjecting stents to 60 seconds UV with standard filter.

TABLE 14

| Sample No. | Heparin Coating Composition | | | | | | Pre-photo | Post-photo | Heparin Activity MU/cm$^2$ |
|---|---|---|---|---|---|---|---|---|---|
| | Reagent (mg/mL) | | | Solvent (%) | | | | | |
| | pBMA | photo-PVP | photo-heparin | THF | IPA | H$_2$O | | | |
| 13-A | 10 | (−) | (−)* | 90 | (−) | 10 | (+) | (−) | 9 |
| 13-B | 5 | 0.625 | (−)** | 50 | 40 | 10 | (+) | (−) | 7 |
| 13-C | 5 | 0.625 | (−)** | 50 | 40 | 10 | (−) | (−) | 9 |
| 13-D | 10 | (−) | 5 | 90 | (−) | 10 | (−) | (−) | 4 |
| 13-E | 5 | 0.625 | 0.625 | 50 | 40 | 10 | (−) | (−) | 3 |
| 13-F | 10 | (−) | 5 | 90 | (−) | 10 | (+) | (−) | 5 |
| 13-G | 5 | 0.625 | 0.625 | 50 | 40 | 10 | (+) | (−) | 30 |
| 13-H | 5 | 0.625 | 0.625 | 50 | 40 | 10 | (+) | (−) | 33 |
| 13-I | 5 | 0.625 | 0.625 | 50 | 40 | 10 | (−) | (+) | 30 |

*Na-heparin @ 5 mg/mL was substituted for photo-heparin
**Na-heparin @ 0.625 mg/mL was substituted for photo-heparin These results show that biocompatible layer having excellent heparin activity can be formed by pre-irradiating the heparin coating composition prior to depositing the composition on the surface of the coated article. Pre-irradiation gave the same heparin activity as stents having compositions that were post-irradiated.

Example 14

Heparin activity was tested on the surface of stents having a coating of polylactic acid with a rapamycin analog that were coated with various heparin-containing compositions, wherein the compositions were subject to irradiation after the compositions were spray coated (or solution coated where indicated) onto the surface of the stents. Irradiation was performed by subjecting the heparin-containing composition to UV (filtered using an Edmund 407 filter) for 60 seconds.

The photo-crosslinker (Compound IV; TBBE) was used at a concentration in the range of 1-5 mg/mL. PLA was used at a concentration in a range of 1-10 mg/mL. Top coats of photo-heparin (alone) were applied in water at a concentration of 50 mg/mL.

TABLE 15

| Sample No. | Coating | | Heparin Activity MU/cm$^2$ |
|---|---|---|---|
| | First Coat | Second Coat | |
| 14-A1 | Photo-PVP in solution UV (filtered) | Photo-PVP/PLA/photo-heparin UV (filtered) | 42 |
| 14-A2 | Photo-PVP in solution UV (filtered) | Photo-PVP/PLA/photo-heparin UV (filtered) | 41 |
| 14-B1 | Photo-crosslinker spray (THF) UV (filtered) | Photo-heparin (THF/Water) spray, UV (filtered) | 53 |
| 14-B2 | Photo-crosslinker spray (THF) UV (filtered) | Photo-heparin (THF/Water) spray, UV (filtered) | 45 |

TABLE 15-continued

| Sample No. | Coating | | Heparin Activity MU/cm² |
|---|---|---|---|
| | First Coat | Second Coat | |
| 14-C1 | Photo-crosslinker spray (THF) UV (filtered) | Photo-heparin (Water) spray, UV (filtered) | 12 |
| 14-C2 | Photo-crosslinker spray (THF) UV (filtered) | Photo-heparin (Water) spray, UV (filtered) | 11 |
| 14-D1 | Photo-PVP/PLA/photo-heparin spray UV (filtered) | Photo-heparin (THF/Water) spray, UV (filtered) | 45 |
| 14-D2 | Photo-PVP/PLA/photo-heparin spray UV (filtered) | Photo-heparin (THF/Water) spray, UV (filtered) | 46 |
| 14-E1 | Photo-PVP/PLA/photo-heparin spray UV (filtered) | (—) | 46 |
| 14-E2 | Photo-PVP/PLA/photo-heparin spray UV (filtered) | (—) | 46 |

Similar to previous results, these results also show that biocompatible layer having excellent heparin activity can be formed by pre-irradiating the heparin coating composition prior to depositing the composition on the surface of the coated article. These results also show that biocompatible layer having excellent heparin activity can be formed using on a biodegradable layer. These results also show that a non-water soluble photo-crosslinker can be used to promote the formation of a layer with heparin activity, wherein the photo-heparin is applied in a binary solvent system.

Example 15

Heparin activity was tested on the surface of stents that were coated with various heparin-containing compositions, wherein the compositions were subject to irradiation before the compositions (pre-irradiation) were spray coated onto the surface of the stents.

The stents were prepared, as indicated above, were (I) silane-treated and had a (II) Parylene™ base layer, (III) a pBMA/pEVA/rapamycin layer, (IV) a pBMA layer, and (V) a pBMA/photo-heparin/photo-PVP (as indicated in Table 16).

Stents were subject to mechanical testing as described in Example 9.

Pre-irradiation was performed by subjecting the heparin-containing composition to UV (non-filtered) for 4 times irradiation for 99 seconds per time. Using a Dymax light without the filter (greater than 25 mU/cm2)

TABLE 16

| | Heparin Coating Composition | | | | | | | | Heparin Activity |
|---|---|---|---|---|---|---|---|---|---|
| | Reagent (mg/mL) | | | Solvent (%) | | | | | |
| Sample No. | pBMA | photo-PVP | photo-heparin | THF | IPA | H₂O | Expanded | Wash | MU/cm² (mean) |
| 15-A | 5 | 0.625 | 0.625 | 50 | 40 | 10 | (+) | Plasma | 22 |
| 15-B | 5 | 0.625 | 0.625 | 50 | 40 | 10 | (−) | PBS | 37 |
| 15-C | 5 | 0.1 | 0.1 | <90* | <10* | <1 | (+) | Plasma | 5 |
| 15-D | 5 | 0.1 | 0.1 | <90* | <10* | <1 | (−) | PBS | 6 |
| 15-E | 5 | 0.5 | 0.1 | <90* | <10* | <1 | (+) | Plasma | 5 |
| 15-F | 5 | 0.5 | 0.1 | <90* | <10* | <1 | (−) | PBS | 7 |
| 15-G | 5 | 0.1 | 0.5 | 79.2 | 19.8 | <1 | (+) | Plasma | 26 |
| 15-H | 5 | 0.1 | 0.5 | 79.2 | 19.8 | <1 | (−) | PBS | 29 |
| 15-I | 5 | 0.5 | 0.5 | 79.2 | 19.8 | <1 | (+) | Plasma | 39 |
| 15-J | 5 | 0.5 | 0.5 | 79.2 | 19.8 | <1 | (−) | PBS | 34 |
| 15-K | 20 | 0.4 | 0.4 | 79.2 | 19.8 | <1 | (+) | Plasma | 4 |
| 15-L | 20 | 0.4 | 0.4 | 79.2 | 19.8 | <1 | (−) | PBS | 7 |

*THF and IPA were lower than the indicated values to allow for a small amount of water in the solvent system These results show that optimal durability and heparin activity (15G-I) was seen when the amount of water was reduced to very low concentrations in the solvent (<1%). This allowed for higher concentrations of pBMA in the mixture, which provided excellent durability. Low concentrations of photo-heparin in Samples 15C-F were believed to cause the low heparin activity.

The invention claimed is:

1. A medical article having a bioactive agent-releasing coating having heparin activity, the coating comprising:
    (a) a first coated layer comprising a bioactive agent; and
    (b) a second coated layer formed from a second coating composition comprising heparin, photoreactive groups, and a polymeric material, wherein the second coating composition is irradiated prior to being disposed to form the second coated layer.

2. The medical article of claim 1 wherein the first coated layer comprises a hydrophobic polymer.

3. The medical article of claim 2 wherein the hydrophobic polymer of the first coated layer is selected from the group of poly(alkyl(meth)acrylates).

4. The medical article of claim 3 wherein the hydrophobic polymer of the first coated layer is poly(butyl(meth)acrylate).

5. The medical article of claim 2 wherein the first coated layer further comprises a polymer that is different than, but can be blended with, the hydrophobic polymer.

6. The medical article of claim 5 wherein the first coated layer further comprises poly(ethylene-co-vinyl acetate).

7. The medical article of claim 1 wherein the polymeric material of the second coated layer comprises a hydrophobic polymer.

8. The medical article of claim 7 wherein the hydrophobic polymer of the first coated layer and the hydrophobic polymer of the second coated layer are the same.

9. The medical article of claim 1 wherein the bioactive agent is selected from the group consisting of anti-proliferative agents, an anti-mitotics, and antibiotics.

10. The medical article of claim 9 wherein the bioactive agent is selected from rapamycin and analogs thereof.

11. The medical article of claim 1 wherein the photoreactive groups are pendent from heparin.

12. The medical article of claim 1 wherein the second coated layer further comprises a component selected from the group consisting of polyvinylpyrrolidone, polyethylene glycol, polyethylene glycol sulfonates, fatty quaternary amines, fatty sulfonates, fatty acids, dextran, dextrin, and cyclodextrin.

13. The medical article of claim 12 wherein the second coated layer comprises polyvinylpyrrolidone.

14. The medical article of claim 12 wherein photoreactive groups are pendent from a component selected from the group consisting of polyvinylpyrrolidone, polyethylene glycol, polyethylene glycol sulfonates, fatty quaternary amines, fatty sulfonates, fatty acids, dextran, dextrin, and cyclodextrin.

15. The medical article of claim 14 wherein the photoreactive groups are pendent from polyvinylpyrrolidone.

16. The medical article of claim 15 wherein the photoreactive groups are pendent from both heparin and poly(vinylpyrrolidone).

17. The medical article of claim 1 being an intraluminal prosthesis.

18. The medical article of claim 17 being a stent.

19. The medical article of claim 1 comprising a third coated layer comprising a polymeric material, wherein the third coated layer is either between the first coated layer and the surface, or between the first coated layer and the second coated layer.

20. A method for preparing a medical article having a bioactive agent-releasing coating with heparin activity, comprising the steps of:
 (a) providing a medical article having a first coated layer comprising a bioactive agent; and
 (b) irradiating a composition comprising heparin, photoreactive groups, and polymeric material to activate the photoreactive groups;
 (c) after step (b), disposing the irradiated composition on the first coated layer.

21. A medical article having a bioactive agent-releasing coating having heparin activity of 10 mU/cm$^2$ or greater, the coating comprising:
 (a) biostable or biodegradable polymer;
 (b) bioactive agent;
 (c) heparin, and
 (d) photoreactive groups, wherein the photoreactive groups are activated prior to being placed in contact with the medical article.

22. A medical article having a bioactive agent-releasing coating comprising:
 (a) hydrophobic polymer
 (b) bioactive agent;
 (c) heparin;
 (d) photoreactive groups; and
 (e) a component selected from the group consisting of polyvinylpyrrolidone, polyethylene glycol, polyethylene glycol sulfonates, fatty quaternary amines, fatty sulfonates, fatty acids, dextran, dextrin, and cyclodextrin.

* * * * *